(12) United States Patent
Goodlett et al.

(10) Patent No.: US 9,273,339 B2
(45) Date of Patent: Mar. 1, 2016

(54) METHODS FOR IDENTIFYING BACTERIA

(75) Inventors: David R. Goodlett, Seattle, WA (US);
Robert K. Ernst, Silver Spring, MD (US); Ying Sonia Ting, Seattle, WA (US); Yu Chieh "Philip" Kao, Seattle, WA (US)

(73) Assignees: UNIVERSITY OF MARYLAND, BALTIMORE, Baltimore, MD (US); UNIVERSITY OF WASHINGTON, Seattle, WA (US)

( * ) Notice: Subject to any disclaimer, the term of this patent is extended or adjusted under 35 U.S.C. 154(b) by 230 days.

(21) Appl. No.: 13/342,694

(22) Filed: Jan. 3, 2012

(65) Prior Publication Data
US 2012/0197535 A1  Aug. 2, 2012

Related U.S. Application Data

(60) Provisional application No. 61/429,396, filed on Jan. 3, 2011, provisional application No. 61/530,483, filed on Sep. 2, 2011.

(51) Int. Cl.
*G01N 33/48* (2006.01)
*C12Q 1/04* (2006.01)
*G06F 19/14* (2011.01)
*G06F 19/28* (2011.01)
*G06G 7/58* (2006.01)
*H01J 49/00* (2006.01)

(52) U.S. Cl.
CPC *C12Q 1/04* (2013.01); *G06F 19/14* (2013.01); *G06F 19/28* (2013.01); *H01J 49/004* (2013.01)

(58) Field of Classification Search
CPC .................................. G06F 19/14; G06F 19/28
See application file for complete search history.

(56) References Cited

U.S. PATENT DOCUMENTS

| | | | |
|---|---|---|---|
| 7,070,949 | B2 | 7/2006 | Suckau et al. |
| 7,396,686 | B2 | 7/2008 | Suckau et al. |
| 7,805,253 | B2 | 9/2010 | Chen et al. |
| 7,838,824 | B2 | 11/2010 | Vestal |
| 2004/0197826 | A1 | 10/2004 | Suckau et al. |
| 2008/0009029 | A1 | 1/2008 | Govorun et al. |
| 2008/0093547 | A1 | 4/2008 | Hartmer |
| 2009/0095903 | A1 | 4/2009 | Holle |
| 2010/0237238 | A1 | 9/2010 | Franzen |
| 2011/0275113 | A1 | 11/2011 | Kostrzewa et al. |

FOREIGN PATENT DOCUMENTS

| | | |
|---|---|---|
| WO | 2011/060369 | 5/2011 |
| WO | 2014/035270 | 3/2014 |

OTHER PUBLICATIONS van Baar et al. "Characterisation of bacteria by matrix-assisted laser desorption/ionization and electrospray mass spectrometry" FEMS Microbiology Reviews 24 (2000), pp. 193-219.*
Morath et al. "Structure-Function Relationship of Cytokine Induction by Lipteichoic Acid from *Staphylococcus aureus*" JEM (2001) vol. 193, No. 3, pp. 393-398.*
Vaidyanathan et al. "Glow-Injection Electrospray Ionization Mass Spectroscopy of Crude Cell Extracts for High-Throughput Bacterial Identification" American Society for Mass Spectrometry (2002) vol. 13, pp. 118-128.*
Purvine (2003) Proteomics, 3:847-850.
Venable (2004) Nature Methods, 1(1):39-45.
Shaffer (2007) JASMS, 18(6):1080-1092.
Sauer, et al., PLoS ONE, 3(7):e2843.
Panchaud (2009) Anal Chem, 81:6481-8.
El Hamidi (2005) J Lipid Res, 46:1773-1778.
Du (2006) Bioinformatics, 22(17):2059-2065.
Miller, (2005) Nat Rev Microbiol, 3(1): 36-46.
Raetz, (2002) Annu Rev Biochem, 71: 635-700.
Ernst, (1999) Science, 286(5444):1561-5.
Ernst, (2003) J Endotoxin Res, 9(6): 395-400.
Hornef, (2002) Nat Immunol, 3(11):1033-40.
Coats, (2009) Cell Microbiol, 11(11): 1587-99.
Schneiter, (1999) J Cell Bioi, 146(4):741-54.
Han, (2005) Mass Spectrom Rev, 24(3): 367-412.
Jones, (2008) Proc Natl Acad Sci USA, 105(35):12742-7.
Jones, (2010) J Am Soc Mass Spectrom, 21(5): 785-99.
Wenk, (2005) Nat Rev Drug Discov, 4(7): 594-610.
Schwudke, (2006) Anal Chem, 78(2): 585-95.
Leavell, (2006) Anal Chem, 78(15): 5497-503.
Ekroos, (2002) Anal Chem, 74(5): 941-9.
Ejsing, (2006) Anal Chem, 78(17): 6202-14.
Song, (2007) J Am Soc Mass Spectrom, 18(10): 1848-58.
Hubner, (2009) J Mass Spectrom, 44(12): 1676-83.
Yang, (2009) Anal Chem, 81(11): 4356-68.
Han, (2005) Expert Rev Proteomics, 2(2): 253-64.
Han, (2004) Anal Biochem, 330(2): 317-31.
Mikhail, (2005) Anal Biochem, 340(2): 303-16.
Schilling, (2007) Anal Chem, 79(3): 1034-42.
Une, (1984) Infect Immun, 43(3): 895-900.
Wang, (2006) J Biol Chem, 281(14): 9321-30.
Westphal, (1965) Methods Carbohydr. Chem, (5): 83-91.
Caroff, (1988( Carbohydr Res, 175(2): 273-82.
Domon, (1988) Glycoconjugate Journal, 5: 397-409.
Eng, (1994) J Am Soc Mass Spectrom, 5(11): 976-989.
Eng, (2008) J Proteome Res, 7(10): 4598-602.
Moore, (2002) J Am Soc Mass Spectrom, 13(4): 378-86.

(Continued)

*Primary Examiner* — Eric S Dejong

(74) *Attorney, Agent, or Firm* — Wenderoth, Lind & Ponack, LLP

(57) ABSTRACT

The present invention provides methods for identifying bacteria by analysis of lipid A and/or lipoteichoic acid structure and/or mass spectrometry ionization patterns.

10 Claims, 17 Drawing Sheets

(56) References Cited

OTHER PUBLICATIONS

Klammer, (2006) J Proteome Res, 5(3): 695-700.
Park, (2008) J Proteome Res, 7(7): 3022-7.
Rebeil, (2004) Mol Microbiol, 52(5): 1363-73.
Kawahara, (2002) Infect Immun, 70(8): 4092-8.
Knirel, (2005) Biochemistry, 44(5): 1731-43.
Makhoul, (1999) Performance Measures for Information Extraction, 249-254.
Park, (2009) Nature, 458(7242): 1191-5.
Elssner (2005) "Microorganism Identification Based on MALDI-TOF MS Fingerprints," MALDI-Biotyper Microorganism Identification.
Suckau, et al., (2003) Anal Bioanal Chem, 376:952-965.

* cited by examiner

METHODS FOR IDENTIFYING BACTERIA

CROSS-REFERENCE

This application claims priority to U.S. Provisional Patent Application Ser. Nos. 61/429,396 filed Jan. 3, 2011, and 61/530,483 filed Sep. 2, 2011, which are incorporated by reference herein in their entirety.

STATEMENT OF U.S GOVERNMENT INTEREST

This invention was made with government support under 5 U54 AI057141-03 awarded by National Institutes of Health (NIH)—Federal Reporting. The government has certain rights in the invention.

BACKGROUND

Rapid and accurate pathogen identification is needed to allow physicians to react and respond appropriately to infections, including those that are potentially life threatening. Currently, pathogen identification requires culture on solid medium (agar-based plate), followed by diagnostic analysis that normally requires additional rounds of replication in culture or purification of a specific bacterial product. At best, microbe identification requires multiple days during which additional levels of biosafety containment may be required depending on the overall classification of the pathogen. Thus, improved methods for bacterial identification are needed.

SUMMARY OF THE INVENTION

In a first aspect, the invention provides methods for identifying bacteria, comprising
(a) obtaining precursor ion mass spectrometry (PIMS) spectra on precursor ions for lipid A (LA) or precursors molecules thereof and/or lipoteichoic acid (LTA) or precursor molecules thereof, from a sample containing bacteria of interest;
(b) comparing the PIMS spectra to a database of bacterial LA and/or LTA precursor ion mass spectrometry spectra;
wherein the comparing is used to identify bacteria in the sample.

As disclosed herein, the inventors have surprisingly discovered that the methods of the invention can be used, for example, to distinguish bacteria and to distinguish antibiotic vs. non-antibiotic resistant bacteria, and to identify bacterial environmental variants. As such, the present invention will find wide use in a variety of diagnostic and research applications.

In one embodiment, the methods comprise comparing precursor ion m/z values and relative abundance of the precursor ions to the database of bacterial LA and/or LTA precursor ion mass spectrometry spectra data. In another embodiment, the methods further comprise fragmenting all or a subset of the precursor ions to produce an $MS^E$ set of ions, and obtaining MS spectra on all or a subset of the $MS^E$ set of ions ($MS^E$ MS) spectra, and wherein the comparing further comprises comparing the $MS^E$ MS spectra to bacterial LA and LTA $MS^E$ spectra in the database to assist in identifying bacteria in the sample. In a further embodiment, the methods further comprise fragmenting all or a subset of the precursor ions to produce a set of derived fragment ions, and obtaining MS spectra on all or a subset of the derived fragment ions ($MS^n$) spectra, and wherein the comparing further comprises sequentially comparing the $MS^n$ spectra to bacterial LA and LTA $MS^n$ spectra in the database to assist in identifying bacteria in the sample. In another embodiment, the methods further comprise searching the precursor ion and/or $MS^n$ spectra against a database of bacterial LA and LTA signature ions to identify signature ions in the precursor ion and/or $MS^n$ spectra. The methods may further comprise
(i) searching neutral losses of signature ions in the $MS^n$ spectra against a theoretical neutral loss database to identify dissociation formulae;
(ii) proposing LA and/or LTA candidate structures from bacteria in the sample based on the dissociation formulae and the signature ions in the $MS^n$ spectra;
(iii) assigning a score to each LA and/or LTA candidate structure based on correlation between theoretical and acquired $MS^n$ spectra, wherein candidate structures that meet or exceed a user-defined threshold are considered as accurate assignments.

In one embodiment, step (i) comprises
(A) determining a neutral loss of every $MS^n$ spectrum's precursor ion in the corresponding $MS^{n-1}$ spectrum and searching against the theoretical neutral loss database; and
(B) iteratively repeating step (A) until level $MS^1$ is reached; and
wherein step (ii) comprises proposing the LA and/or the LTA structures from the bacteria in the sample based on the integrating data from each $MS^n$ level.

In another embodiment, step (iii) comprises
(A) fragmenting the LA and/or the LTA candidate structures by direct bond cleavage to produce fragmentations;
(B) combining the fragmentations into a reconstructed mass spectra representing the theoretical dissociation of the LA and/or the LTA candidate structures; and
(C) assigning the score to each of the LA and/or the LTA candidate structure based on correlation between theoretical $MS^n$ spectra and the reconstructed mass spectra.

In a second aspect, the present invention provides methods for identifying antibiotic-resistant Gram-negative bacteria, comprising obtaining lipid A from a Gram-negative bacterial sample and determining whether the lipid A comprises a phosphoethanolamine (PEtN) modification, wherein presence of PEtN modified-lipid A indicates that the Gram-negative bacteria is antibiotic-resistant. In one embodiment, the antibiotic resistance comprises resistance to colistin. In a further embodiment, the Gram-negative bacterial sample is selected from the group consisting of an *Acetinotbacter* sample and a *Klebsiella* sample. In a further embodiment, the Gram-negative bacterial sample comprises an *A. baumannii* sample. In a still further embodiment, the Gram-negative bacterial sample comprises a *K. pneumoniae* sample.

In a third aspect, the present invention provides methods for constructing libraries of LA and/or LTA precursor ion and $MS^E$ and/or $MS^n$ data, comprising
(a) obtaining PIMS spectra on precursor ions for lipid A (LA) or precursors molecules thereof and/or lipoteichoic acid (LTA) or precursor molecules thereof obtained from a plurality of different bacteria;
(b) determining precursor ion m/z values and relative ratios of precursor ion signals relative to each other;
(c) determining consensus values for the precursor ion m/z values and the relative ratios of the precursor ion signals relative to each other for a given bacteria; and
(d) storing the consensus values in a database as a feature of the bacteria type.

DETAILED DESCRIPTION OF THE INVENTION

Figure 1:
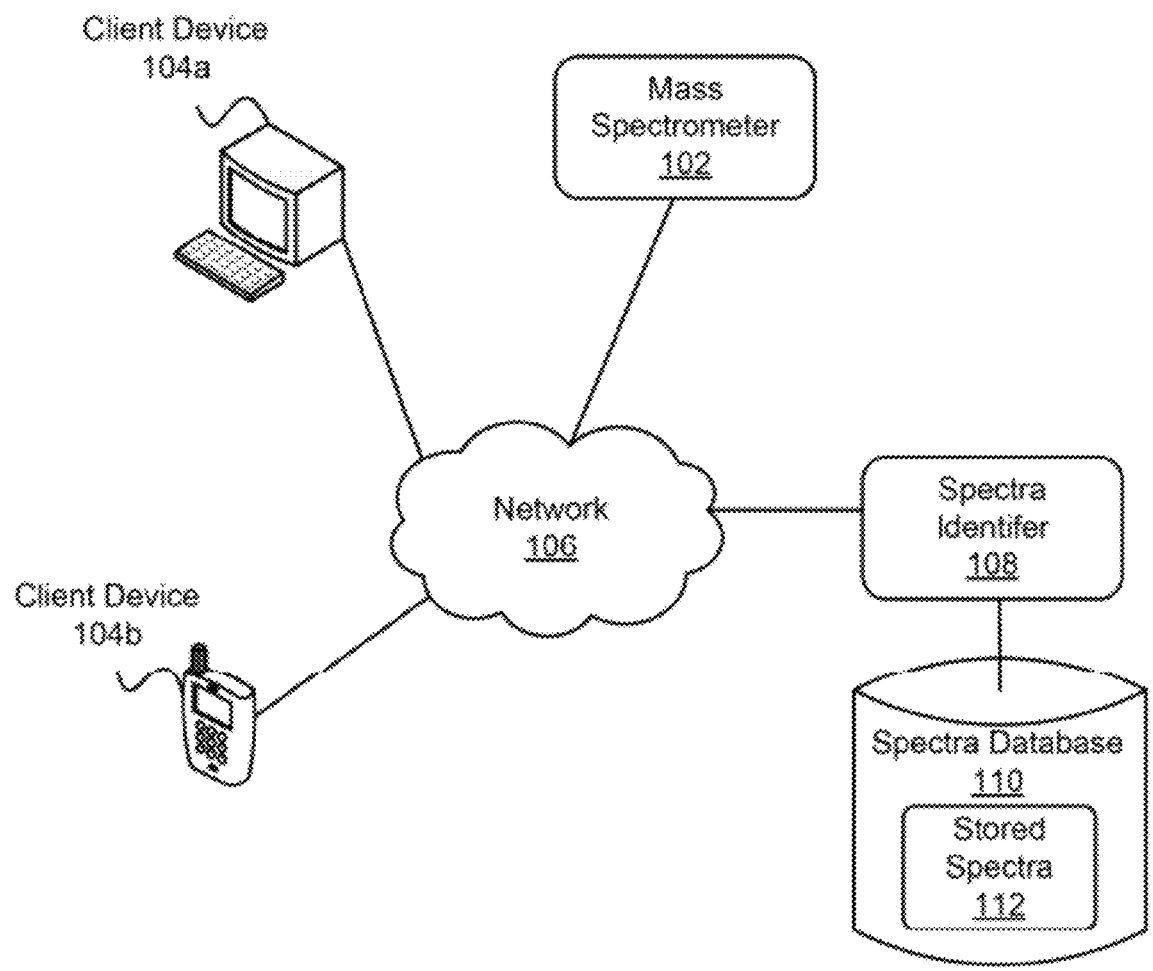
FIG. 1 shows spectra identifier 108 configured to communicate, via network 106, with mass spectrometer 102 and client devices 104a, 104b.

All references cited are herein incorporated by reference in their entirety. As used herein, the singular forms "a", "an" and "the" include plural referents unless the context clearly dictates otherwise. "And" as used herein is interchangeably used with "or" unless expressly stated otherwise. All embodiments of any aspect of the invention can be used in combination, unless the context clearly dictates otherwise.

In a first aspect, the present invention provides methods for identifying bacteria, comprising (a) obtaining precursor ion mass spectrometry (PIMS) spectra on precursor ions for lipid A (LA) or precursors molecules thereof and/or lipoteichoic acid (LTA) or precursor molecules thereof, from a sample containing bacteria of interest;

(b) comparing the PIMS spectra to a database of bacterial LA and LTA precursor ion mass spectrometry spectra; wherein the comparing is used to identify bacteria in the sample.

As disclosed herein, the inventors have surprisingly discovered that the methods of the invention can be used, for example, to distinguish bacteria and to distinguish antibiotic vs. non-antibiotic resistant bacteria, and to identify bacterial environmental variants. As such, the present invention will find wide use in a variety of diagnostic and research applications.

Lipid A, the endotoxic portion of lipopolysaccharide (LPS) is embedded in the outer leaflet of the Gram-negative bacterial outer membrane. As an essential component of Gram-negative bacterial membranes, lipid A exhibits species-specific structural diversity. The general structure consists of a backbone of two glucosamine residues present as a β-(1-6)-linked dimer. This backbone can be diversified in response to specific environmental signals or between bacterial species. Specifically, changes in the fatty acid content varying both in the length and number of fatty acid side chains (e.g. tetra- to hepta-acylated) and phosphorylation patterns can differ as well. Additional modifications of the phosphate residues by monosaccharides, such as aminoarabinose or galactosamine and phosphoethanolamine can occur. The diversity of such species and environmentally-driven structural modifications are an adaptive mechanism that increases bacterial survival often through increasing resistance to host antimicrobial peptides, or in the avoidance of the host innate immune system. Precursor molecules (ie: molecules from which LA is cleaved during isolation) to LA include, but are not limited to LPS.

Lipoteichoic acid (LTA) is a major cell wall component of Gram-positive bacteria. The Gram-positive cell wall is composed of cross-linked peptidoglycan (PG) variably decorated with teichoic acid polymers. Teichoic acid polymers are also linked to plasma membrane phospholipids. The general structure of LTA varies between species consisting of 2 or 4 acyl groups, of variable chain length. LTA from low G+C subdivisions of Gram-positive bacteria contains two fatty acid tails, while those from high G+C bacteria contain 4 fatty acid tails. Additionally, LTA can be variably modified with alanine (in response to low pH), or glycosyl linkages depending on bacterial background. Glycosyl linkages can include glycerolphosphate, galactose, or N-acetyl-glycerol.

The sample may be any suitable sample of interest that is believed to contain bacteria to be identified. The bacteria may be dead or alive, as LA and LTA are quite stable. Non-limiting examples of test samples include, but are not limited to water samples (including but not limited to water samples from ponds, streams, lakes, oceans, seas, wastewater, reservoirs, drinking water, water distribution pipeline, etc.), body fluid samples (including but not limited to wound secretions/scrapings, blood, urine, sweat, saliva, vaginal secretions, sputum), beverage samples, liquid medicine samples, food samples, environmental samples (for example, from, medical centers such as linens, medical devices, etc.); pharmaceutical facilities (for example, from, manufacturing or processing lines); food production facilities; livestock facilities; solid waste samples, diagnostic samples, air, air filters, air duct and breath samples.

The sample can be used as obtained, or can be processed in any way suitable for use with the methods of the invention. In one embodiment, the methods comprise identifying bacteria directly from a complex sample (ie: no requirement for amplifying bacteria present in the sample). In another embodiment, bacteria are isolated from the sample, such as by streaking onto solid bacterial culture medium, followed by growth for an appropriate period of time and use of individual colonies for isolation of LA or LTA, or for initiating a larger-scale culture (for example, an overnight liquid culture) which is then subjected to LA or LTA isolation. It is within the level of skill in the art, based on the teachings herein, to determine an appropriate strategy for processing the sample for a specific use.

In one embodiment, bacterial cells are placed in the mass spectrometer for analysis, with no purification of LA or LTA. In a preferred embodiment, the LA and/or LTA (and precursors thereof) can be isolated from bacteria in the sample using any suitable method that serves to maintain LA and/or LTA structure. As used herein, "isolation" means that LA and/or LTA are separated from their normal cellular environment. The methods do not require the use of purified LA or LTA. In preferred embodiments, the LA and/or LTA for use in the methods of the invention makes up at least 10% of the sample subjected to MS analysis; preferably at least 20%, 30%, 40%, 50%, 60%, 70%, 80%, 90%, 95%, 98%, 99%, or 100% of the sample subjected to MS analysis. Such isolation techniques are known to those of skill in the art, including but not limited to the use of various organic solvents (ex: phenol, chloroform, methanol, ethanol, etc.), ammonium hydroxide/isobutyric acid-based protocols, and microwave-assisted enzymatic digestion and detergent-free mild hydrolysis, as described below. For example, after extraction, LTA/lipid A can be isolated from the phenol-based preparations using gentle hydrolysis, which preserves structural elements (e.g., phosphate groups and attached carbohydrate moieties) that are sensitive to harsh acid treatment, or directly for the ammonium hydroxide/isobutyric acid-based as it cleaves the glycosidic linkage between LTA/lipid A and the rest of the glycolipid molecule.

In a further example, a sample preparation method based on microwave-assisted enzymatic digestion and detergent-free mild hydrolysis to isolate LA and/or LTA (and precursors thereof) is applicable to profiling the lipid A structures from as little as 1 μg of dried bacterial cells (approximately the amount in a small bacterial colony obtained from solid growth medium). This technique has been successfully used with a variety of Gram-positive and Gram-negative bacterial species as shown below.

It will be understood by those of skill in the art that methods for isolating LA, LTA, and precursors thereof may differ for bacteria in different samples; some bacteria may require additional growth time for the growth of colonies, and the membrane characteristics of a given bacteria will affect extraction. Based on the teachings herein, it is within the level of skill in the art to determine the appropriate use of solvents, detergents, buffers, microwave power settings, time under irradiation, etc. to carry out the various types of LA, LTA, or precursor extraction.

The methods of the invention comprise obtaining precursor ion mass spectrometry (PIMS) spectra. As is known in the art, mass spectrometry (MS) is an analytical technique that measures the mass-to-charge ratio of charged particles, and can be used for determining the elemental composition of a sample or molecule and elucidating the chemical structures of molecules. MS comprises ionizing chemical compounds to generate charged molecules or molecule fragments and measuring their mass-to-charge ratios. In a typical MS procedure (a) a sample is loaded onto the MS instrument and undergoes vaporization; (b) the components of the sample are ionized by one of a variety of methods, resulting in the formation of ions; (c) the ions are separated according to their mass-to-charge ratio in an analyzer by electrical and magnetic fields; (d) the ions are detected, often by a quantitative method; and (e) the ion signal is processed into mass spectra. Suitable instruments for carrying out MS thus typically comprise (a) an ion source, which can convert gas phase sample molecules into ions (or, in the case of electrospray ionization, move ions that exist in solution into the gas phase); a mass analyzer, which sorts the ions by their masses by applying electromagnetic fields; and (c) a detector, which measures the value of an indicator quantity and thus provides data for calculating the abundances of each ion present.

Any suitable MS instrument can be used in the methods of the invention. Selecting an appropriate MS instrument and protocol can be accomplished by one of skill in the art based on the teachings herein. Non-limiting MS techniques that can be used to carry out the methods of any embodiment or combination of embodiments of the present invention include, but are not limited to, matrix-assisted laser desorption ionization time-of flight MS (MALDI-TOF-MS) platforms, tandem MS, MALDI-TOF-TOF-MS, infusion-based electrospray ionization (ESI) coupled to ion trap tandem mass spectrometry (ITMS$^n$), and any of the many so-called ambient ionization methods such as surface acoustic wave nebulization (SAWN) technology, including SAWN on any mass analyzer (e.g. quadrupole TOF-MS (QTOF) or SAWN-ion trap (IT) MS). Other examples of ambient ionization methods include DESI and DART, but there are numerous such methods available, as will be understood by those of skill in the art.

Surface acoustic waves (SAWs) are Rayleigh waves, and are generated by the application of a voltage across a piezoelectric material, causing a mechanical displacement of the uppermost layer of the chip, which propagates as a "ripple" across the surface of the wafer. At the appropriate frequency, surface acoustic waves can be used to atomize droplets pipetted onto the surface of a lithium niobate wafer. We have previously shown that the SAW nebulized (SAWN) aerosol contains charged molecules that could be sampled by MS to record usable $MS^1$ and $MS^2$ spectra (WO2011/060369). In fact, SAWN generates multiply charged ions similar to those of ESI that can be easily subjected to $MS^n$. The advantage of glycolipid analysis by SAWN over MALDI and ESI are threefold: 1) ionization occurs from a planar device, like MALDI, that circumvents clogging of capillaries and thus facilitating higher throughput and ease of use by non-experts, 2) it is less energetic than ESI and MALDI making it more likely that the native chemical signature we seek to measure will be intact on transfer to the MS, and 3) no chemical matrix is required as is the case with MALDI such that mass spectra free of matrix-based chemical noise are produced down to the low m/z region where glycolipids of interest to this proposal are detected. A planar SAWN device provides the ease of use of MALDI, i.e. a planar surface where samples are simply pipetted, but without need for a matrix that can obscure ions of interest and combines this with the performance of ESI, i.e. multiply charged precursor ions that can be used in, for example, hierarchical tandem mass spectrometry ($MS^n$), as described below.

As used herein, "Precursor ions" are ions of a starting molecule (LA, LTA, and/or precursors thereof) generated during MS. Such precursor ions may also be referred to as $MS^1$ ions. As will be understood by those of skill in the art, MS may result in a large number of precursor ions from a given starting molecule. Obtaining the PIMS spectra does not require obtaining PIMS spectra of all $MS^1$ ions. Thus, in various embodiments, obtaining the PIMS spectra comprises obtaining PIMS spectra on 1, 2, 3, 4, 5, 6, 7, 8, 9, 10, 11, 12, 13, 14, 15, 16, 17, 18, 19, 20, 21, 22, 23, 24, or more $MS^1$ ions. In one non-limiting example, the method comprises obtaining the PIMS spectra for the 1, 2, 3, 4, 5, 6, 7, 8, 9, 10, 11, 12, 13, 14, 15, 16, 17, 18, 19, 20, 21, 22, 23, 24, or more $MS^1$ ions, such as the most predominant ions. In another embodiment, the method comprises obtaining the PIMS spectra on all $MS^1$ ions.

The PIMS spectra provides information on (a) the m/z values of the precursor ions generated, which represents (or reads) a "barcode" for the LA and/or LTA of bacteria in the sample; and (b) the relative abundance of the precursor ions generated. The method further comprises comparing the PIMS spectra to a database of bacterial LA and LTA precursor ion mass spectrometry spectra, to permit identification of bacteria present in the sample based on the comparison. For example, bacterial identifications may occur by reading out simple phenotypes of two measured components for each sample: 1) precursor ion m/z values (mass to charge ratio) which can be used for determining the elemental composition of a sample or molecule and elucidating the chemical structures of molecules, 2) the normalized, relative abundance of these precursor ions, which may represent more subtle differences in the bacterial signature, such as environmental factors and 3) by conducting hierarchical tandem mass spectra on all or a select set of PIMS ions to reveal differences and complexity under $MS^1$ ions composed of multiple entities all with different chemical configurations but the same $MS^1$ value commonly referred to as isobars.

In one embodiment using purified LA and/or LTA, obtaining PIMS spectra on precursor ions comprises selecting peaks between about 1000 m/z and about 2200 m/z; in other embodiments, between about 1100 m/z and about 2100 m/z, or between about 1200 m/z and about 2000 m/z. These embodiments focus the analysis on ions with a mass to charge ratio likely to be of most relevance for the analysis. As will be understood by those of skill in the art, the m/z ranges can vary above or below these values, depending on all relevant factors in a given MS assay (such as degree of purification, instrument, etc.). In embodiments where unpurified LA and/or LTA samples are used, the m/z ranges may be approximately 10 fold higher than those discussed above (ie: between about 10,000 m/z and about 22,000 m/z).

The methods may further comprise various techniques for data processing, as are within the level of skill in the art based on the teachings herein. For example, the methods may comprise weighting and scaling of spectral peaks using any suitable technique. In another non-limiting embodiment, spectral peaks may be binned as a means to reduce costs and computational requirements.

The methods of the invention further comprise comparing the PIMS spectra to a database of bacterial LA and/or LTA precursor ion mass spectrometry spectra, wherein the comparing is used to identify bacteria in the sample. The database may be of any suitable type for a given application. In one embodiment, the database may comprise or consist of LA or LTA precursor ion MS data previously obtained from a single bacterial species (and may include precursor ion MS data a variety of sub-species); this embodiment can be used, for example, in methods designed to determine if a specific bacteria of interest is present in the sample. In another embodiment, the database may comprise or consist of LA and/or PTA precursor ion MS data previously obtained from a plurality of bacteria of interest. In one such embodiment, the database contains LA and/or LTA precursor ion MS data previously obtained from a plurality of Gram-positive bacteria, a plurality of Gram-negative bacteria, or a plurality of Gram-positive and Gram-negative bacteria. In another such embodiment, the database may comprise or consist of precursor ion LA and/or LTA MS data previously obtained from a one or more bacteria known to develop antibiotic resistance, wherein the previously obtain MS data includes data from antibiotic-resistant strains and non-antibiotic resistant strains of the bacteria. As will be understood by those of skill in the art, there are many such variations of databases that can be used in the methods of the invention. A suitable database for use will depend on the specifics of the methods to be carried out, and can be determined by one of skill in the art based on the teachings herein. In another embodiment, the database may comprise or consist of any of the database libraries disclosed herein. In another embodiment, the database may comprise or consist of LA or LTA precursor ion MS data previously obtained from one or more (or all) of the following groups of bacteria, that cannot be distinguished using current ribosomal profiling techniques:

Shigella and E. coli;
S. pneumoniae and S. mitis;
Pseudomonas subspecies including aeruginosa and Stenotrophomonas maltophila; A. baumanii and A. calcoaceticus;
Enterobacter subspecies including E. asburiae, E. cloacae, E. hormaechei, E. kobei, E. ludwigii, and E. nimipressuralis;
Bordetella pertussis and B. bronchiseptica;
Bacteroides nordii and B. salyersiae;
Candida africana and C. albicans;
Acetinotbacter subspecies; and
Methicillin-resistant Staphylococcus aureus (MRSA) strains and non-methicillin resistant Staphylococcus aureus.

The methods of the invention may be used to detect single bacterial cells present in a sample. In various embodiments, at least $10^2$, $10^3$, $10^4$, $10^5$, or $10^6$, bacterial cells are present in the sample.

The data included in the databases includes at least precursor ion m/z values for LA or LTA molecules in the bacteria represented in the database. The data may also include the normalized, relative abundance of these precursor ions, as well as data regarding the MS technique used to generate the data. In a preferred embodiment, the MS technique used to generate the PIMS spectra from the sample is the same as the MS technique used to generate the data in the database. The data may include limited or exhaustive hierarchical tandem mass spectrometry data used to define structures or define subtle differences between species on all or a select set of PIMS ions. The data may further comprise structural information for the LA and/or LTA present in bacteria or sub-species thereof represented in the database.

The database may comprise a single database, or one or more databases that can be separately accessed and may be integrated, as discussed in more detail below.

In another embodiment, the comparison comprises a classification system to provide a score for identification. For example, each database entry can include a probability-based score. This score, perhaps along with other information, can be used to identify an ion, spectrum, LA, or LTA. Any such suitable classification system can be used to provide a score such as a probability based score, and it is well within the level of those of skill in the art to determine an appropriate system based on the teachings herein.

Figure 6:
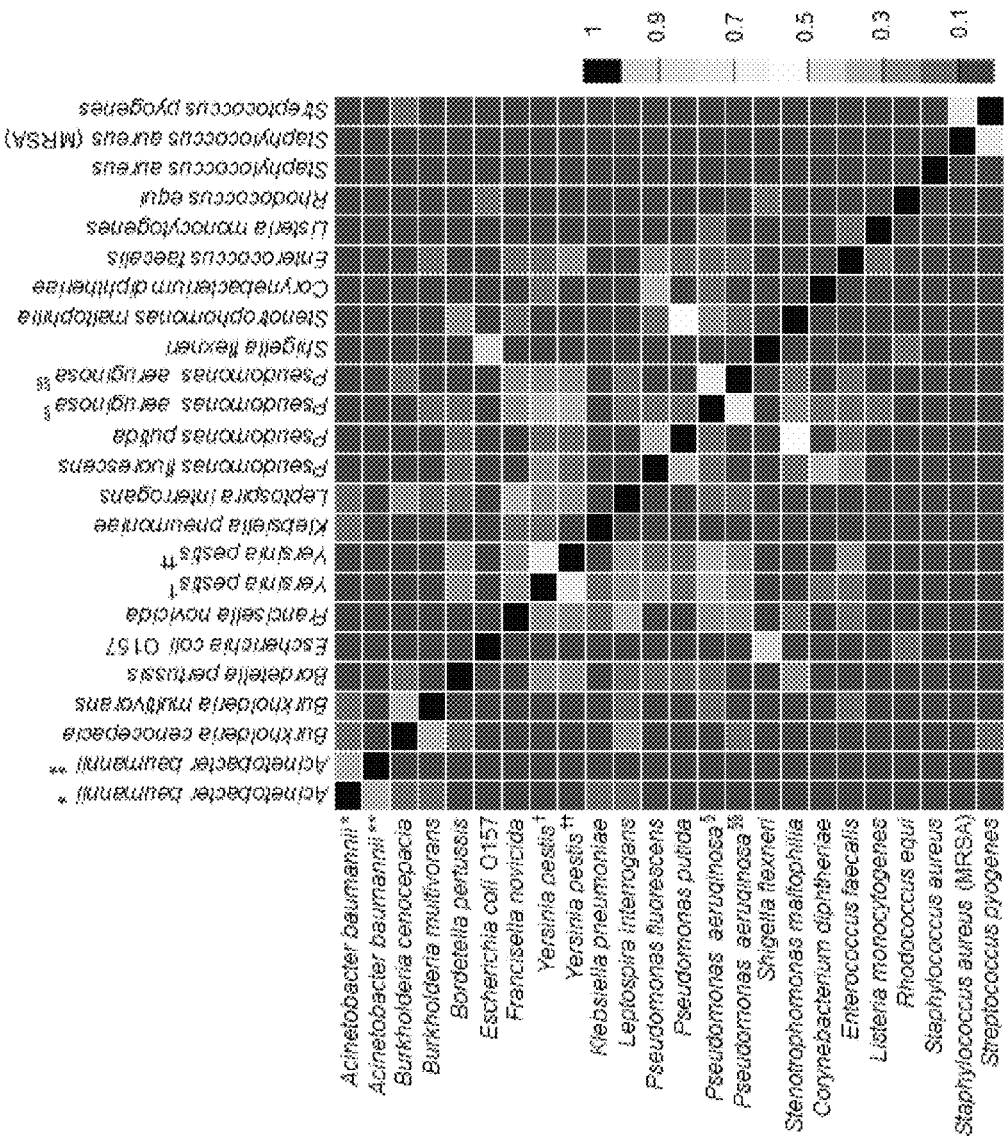
FIG. 6. Heat map demonstrating bacterial identification from MALDI-TOF-MS data of glycolipid extracts. Dot-product comparison of MALDI-TOF MS1 spectra of Gram-negative bacterial Lipid A and Gram-Positive LTA and mixtures shows lipid A and LTA are unique for species, sub-species, and environmental history. Dot-product scores are normalized to values between 0, no match (dark gray), to 1 a perfect match (black). Shades in between indicate that species are similar, but unique. Key: (A): *Acinetobacter baumannii* *; (B): *Acinetobacter baumannii* *; (C): *Burkholderia cenocepacia*; (D): *Burkholderia multivorans*; (E): *Bordetella pertussis*; (F): *Escherichia coli O*157; (G):*Francisella novicida*; (H): *Yersinia pestis* t; (I): *Yersinia pestis* tt; (J): *Klebsiella pneumoniae*; (K): *Leptospira interrogans*; (L): *Pseudomonas fluorescens*; (M): *Pseudomonas putida*; (N): *Pseudomonas aeruqinosa* §;(O): *Pseudomonas aeruqinosa* §§(P): *Shigella flexneri*; (Q): *Stenotrophomonas maltophilia*; (R): *Corynebacterium diphtheriae*; (S): *Enterococcus faecalis*; (T): *Listeria monocytogenes*; (U): *Rhodococcus equi*; (V): *Staphylococcus aureus* ; (W):*Staphylococcus aureus* (MRSA); (X): *Streptococcus phyogenes*.

Any type of comparison of the PIMS spectra to the database MS data can be used to identify bacteria in the sample. For example, any means of comparing the LA and/or precursor ion m/z values in the sample to the m/z values in the database can be used; similarly, any means of comparing the relative abundance of such precursor ions generated from LA and/or LTA in the sample to the data in the database can be used. In one non-limiting embodiment, the comparison may comprise a dot-product comparison of spectra incorporating m/z values and (optionally) their relative intensities. In another embodiment, a heat map comparison of spectra incorporating m/z values and (optionally) their relative intensities can be used. An example heat map is depicted in FIG. 6. It is well within the level of those of skill in the art to determine an appropriate comparison technique based on the teachings herein.

The methods of the invention can be used to identify any bacterial species or sub-species in a sample. Further, the methods can be used to identify multiple bacterial species and/or sub-species from a given sample. In one embodiment, the methods are used to identify Gram-positive bacteria (i.e.: to determine the identity of Gram-positive bacteria in the sample, or to assess the presence of a specific Gram-positive bacteria in the sample). In this embodiment, the method comprises obtaining PIMS spectra on precursor ions for LA. In another embodiment, the methods are used to identify Gram-negative bacteria (ie: to determine the identity of Gram-negative bacteria in the sample, or to assess the presence of a specific Gram-negative bacteria in the sample). In this embodiment, the method comprises obtaining PIMS spectra on precursor ions for LTA. In another embodiment, the methods are to identify unknown bacteria (i.e.: regardless of whether Gram-negative or Gram-positive) in a sample. In this embodiment, the method comprises obtaining PIMS spectra on precursor ions for LA and LTA. It will be recognized by those of skill in the art that methods comprising PIMS spectra on precursor ions for LTA may further comprise obtaining PIMS spectra on precursor ions for LA, while methods comprising PIMS spectra on precursor ions for LA may further comprise obtaining PIMS spectra on precursor ions for LTA.

In various non-limiting embodiments, the methods can be used to identify one or more bacteria (or sub-species thereof) including but not limited to Escherichia coli, Staphylococcus aureus, Staphylococcus epidermidis, Streptococcus pneumoniae, S. mitis, Streptococcus pyogenes, Stenotrophomonas maltophila, Mycobacterium tuberculosis, Neisseria gonorrhoeae, Neisseria meningitidis, Bordetella pertussis, B. bronchioseptica, Enterococcus faecalis, Salmonella typhimurium, Salmonella choleraesuis, Klebsiella pneumoniae, Pseudomonas aeruginosa, Acinetobacter baumannii, A. cal-

*coaceticus, Bacteroides nordii, B. salyersiae, Enterobacter* subspecies including *E. asburiae, E. cloacae, E. hormaechei, E. kobei, E. ludwigii*, and *E. nimipressuralis*, extended spectrum β-lactamase organisms, as well as bacterium in the genus *Acinetobacter, Actinomyces, Bacillus, Bacteroides, Bordetella, Borrelia, Brucella, Clostridium, Corynebacterium, Campylobacter, Deinococcus, Escherichia, Enterobacter, Enterococcus, Erwinia, Eubacterium, Flavobacterium, Francisella, Gluconobacter, Helicobacter, Intrasporangium, Janthinobacterium, Klebsiella, Kingella, Legionella, Leptospira, Mycobacterium, Moraxella, Neisseria, Oscillospira, Proteus, Pseudomonas, Providencia, Rickettsia, Salmonella, Staphylococcus, Shigella, Spirillum, Streptococcus, Stenotrophomonas Treponema, Ureaplasma, Vibrio, Wolinella, Wolbachia, Xanthomonas, Yersinia*, and *Zoogloea*.

Figure 7:
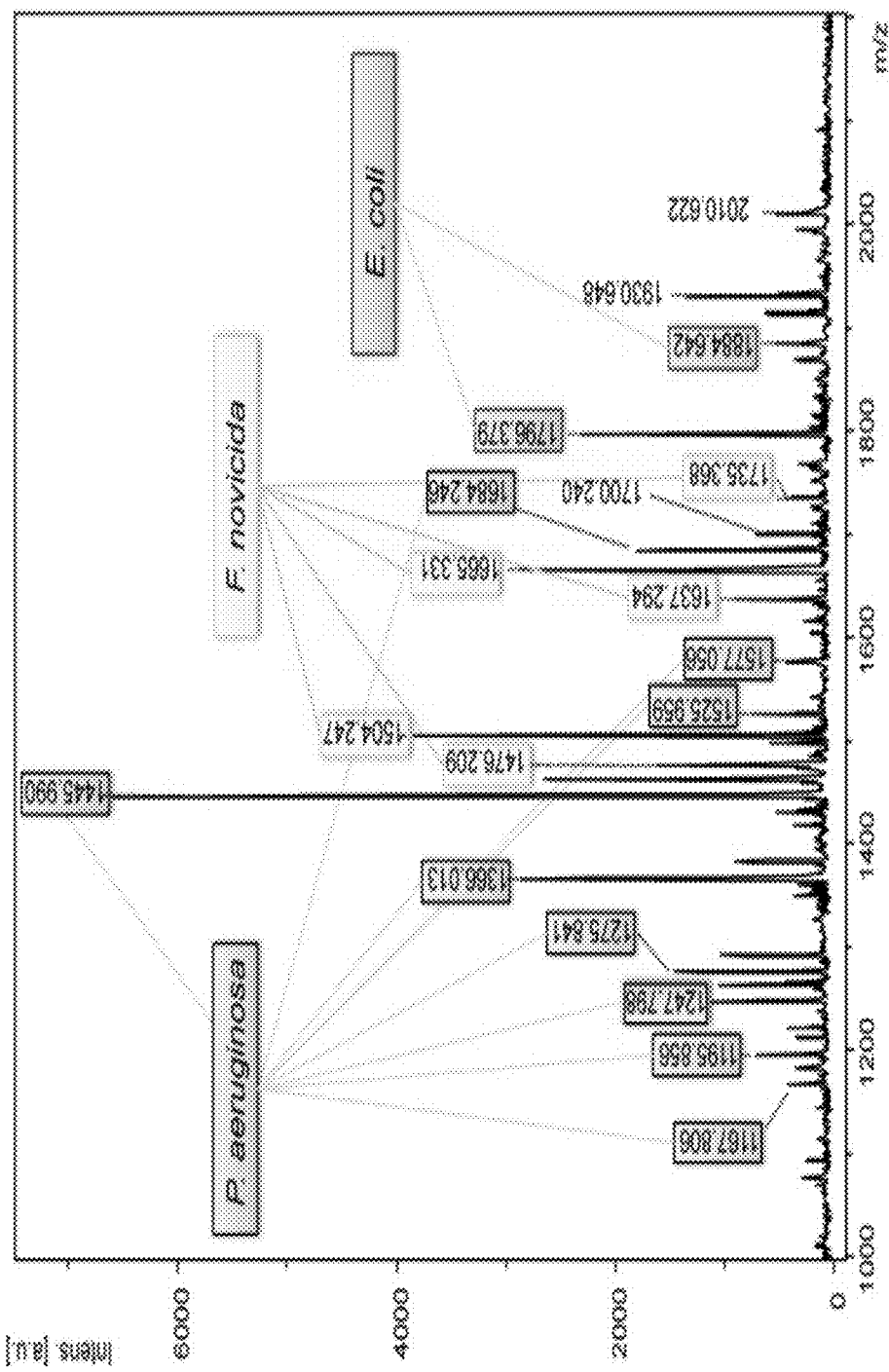
FIG. 7. MALDI-TOF mass spectrum of a mixture of three lipid A extracts. *P. aeruginosa, F. novicida* and *E. coli* lipid A extracts were mixed 10:10:1 and a mass spectrum recorded in negative ion mode on a MALD-TOF-MS (Bruker Autoflex Speed).
Figure 8:
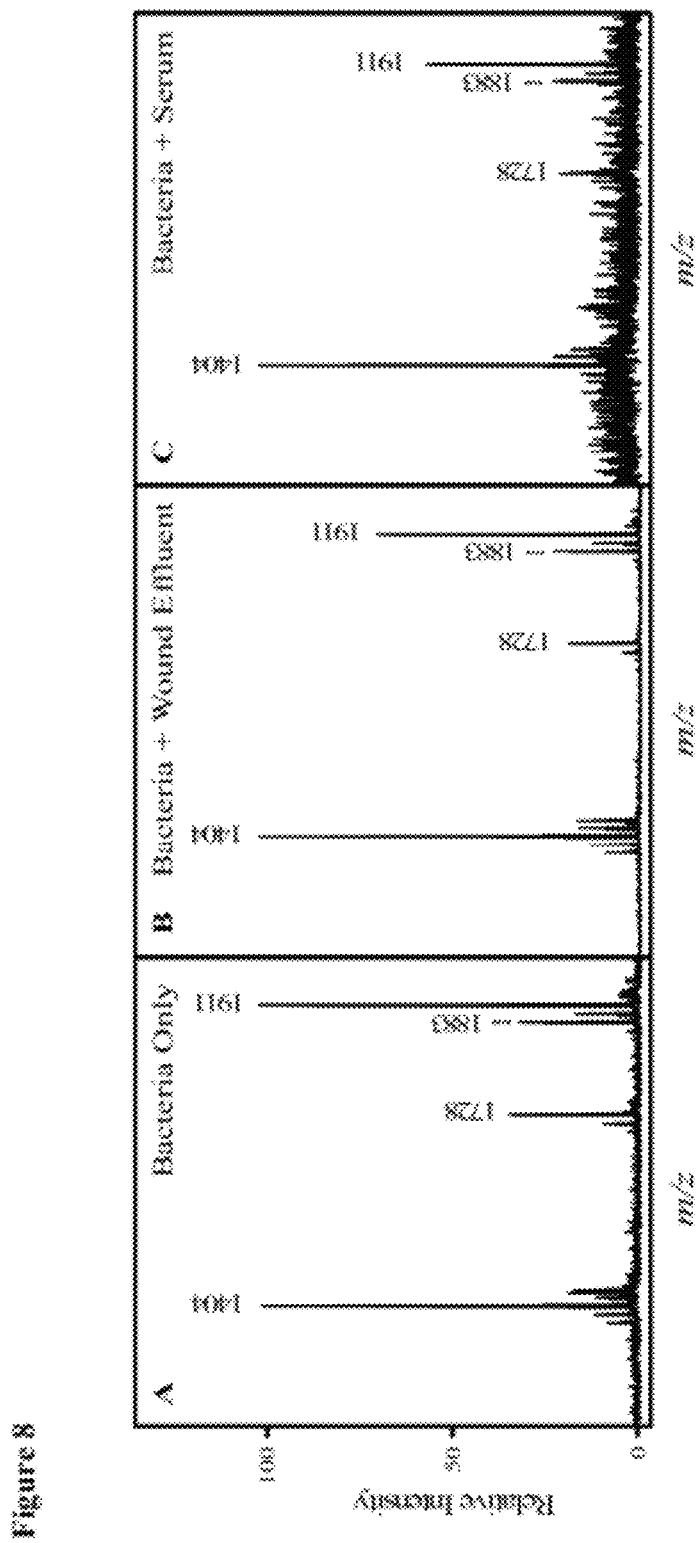
FIG. 8: MALDI-TOF mass spectrum of *A. baumannii* strain 19606 mixed with complex solutions. Approximately 1×10$^8$CFU of *A. baumannii* (50 μl) was resuspended in 50 μl of: (A) 1×PBS, (B) human wound effluent, or (C) human serum. Mass spectrum recorded in negative ion mode on a MALDI-TOF-MS (Bruker Autoflex Speed).
Figure 9:
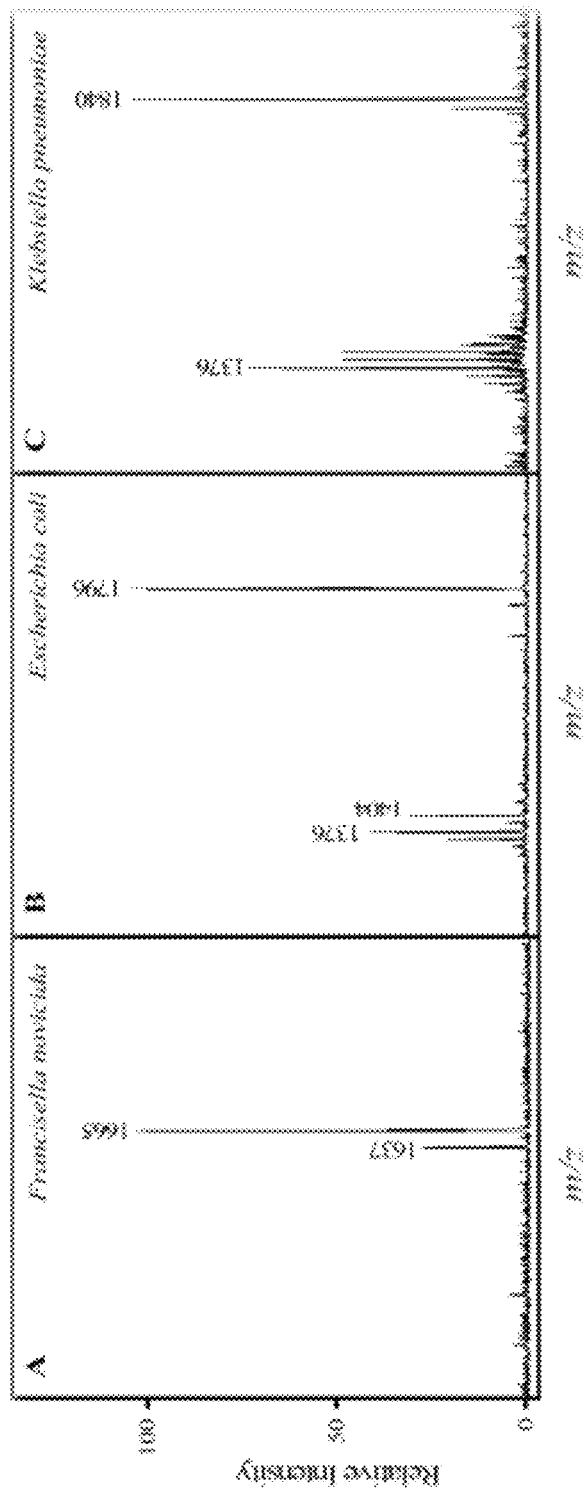
FIG. 9. MALDI-TOF mass spectrum of glycolipids from microwave extracted cells harvested from agar plates. (A) *F. novicida*, (B) *E. coli* (C) *K. pneumoniae*. Mass spectra recorded in negative ion mode on a MALDI-TOF-MS (Bruker Autoflex Speed). Species at m/z 1376-1404 are breakdown products of the major base peaks FIG. 10. Addition of phosphoethanolamine and a currently unidentified hexosamine moiety to *A. baumannii* lipid A are important for resistance to the antimicrobial peptide colistin (polymyxin E). (A) MALDI-TOF mass spectrum and structural characterization of lipid A from *A. baumannii* showing the addition of the terminal positively charged moieties—phosphoethanolamine (PEtN) and hexosamine. Mass spectrum recorded in negative ion mode on a MALDI-TOF-MS. (B) MALDI-TOF-MS Analysis of *A. baumannii* strains from hospitals at the National Institutes of Health, Thailand, and Walter Reed Medical Hospital for the presence of PEtN and hexosamine.

As shown in the examples that follow (see, for example, FIG. 6), analysis of $MS^1$ spectra was used to demonstrate the ability of LA and LTA $MS^1$ data to distinguish not only bacteria, but also antibiotic-resistance (MRSA distinguishable from non-MRSA) and environmental variants (*P. aeruginosa* grown high ($^\S$) and low Mg ($^{\S\S}$) distinguishable) at high sensitivity, accuracy, and specificity. The data (see, for example, FIGS. 7-8) further show that MS1 data can be used to directly identify bacteria in complex samples.

In another embodiment, the method further comprises fragmenting all or a subset of the precursor ions to produce an $MS^E$ set of ions, and obtaining MS spectra on all or a subset of the $MS^E$ set of ions ($MS^E$ MS) spectra, and wherein the comparing further comprises comparing the $MS^E$ MS spectra to bacterial LA and LTA $MS^E$ spectra in the database to assist in identifying bacteria in the sample. Those of skill in the art will understand the types of mass spectrometry devices that are most suitably used with this embodiment of the invention. Any MS device that can fragment ions can produce $MS^E$ spectra. For example, the simplest form of an MS is an ionization device and a mass analyzer and detector. One can modify the way ions are made going from "soft" where mostly MS1 ions are recorded to "hard" where mostly all of the MS1 are fragmented to produce an MSE spectrum. In another embodiment, an ESI-TOF-MS device can be used (See Proteomics 3:847-850 (2003).

As used herein, "$MS^E$" refers to fragmentation of all $MS^1$ ions, or a subset of ions. See, for example, Nature Methods 2004 Oct. 1(1):39-45. This embodiment can be used, for example, if the $MS^1$ data is inconclusive in identifying bacteria present in the sample, and provides a multiplex approach that reveals additional information of bacterial LA/LTA structure.

In various embodiments, obtaining the $MS^E$ MS spectra comprises obtaining $MS^E$ MS spectra on 1, 2, 3, 4, 5, 6, 7, 8, 9, 10, 11, 12, 13, 14, 15, 16, 17, 18, 19, 20, 21, 22, 23, 24, or more $MS^E$ ions. In one non-limiting example, the method comprises obtaining the $MS^E$ MS spectra for the 1, 2, 3, 4, 5, 6, 7, 8, 9, 10, 11, 12, 13, 14, 15, 16, 17, 18, 19, 20, 21, 22, 23, 24, or more of the most abundant $MS^E$ ions. In another embodiment, the method comprises obtaining the $MS^E$ MS spectra on all $MS^E$ ions.

The $MS^E$ MS spectra provides similar information on the $MS^E$ ions as did the PMIS on the precursor ions, including but not limited to information on (a) the m/z values of the $MS^E$ ions assessed; and (b) the relative abundance of the $MS^E$ ions generated. Similarly, the database(s) to be used in this embodiment would further comprise previously obtained $MS^E$ MS spectra data similar to that present in the database for the PIMS spectra, including but not limited to $MS^E$ ion m/z values for LA or LTA molecules in the bacteria represented in the database. The data may also include the normalized, relative abundance of these $MS^E$ ions, scoring information, as available, for the $MS^E$ ions, as well as data regarding the MS technique used to generate the data.

In one embodiment, obtaining $MS^E$ MS spectra on $MS^E$ ions comprises selecting peaks between about 1000 m/z and about 2200 m/z; in other embodiments, between about 1100 m/z and about 2100 m/z, or between about 1200 m/z and about 2000 m/z. These embodiments focus the analysis on $MS^E$ ions with a mass to charge ratio likely to be of most relevance for the analysis.

In another embodiment, the methods further comprise fragmenting all or a subset of the precursor ions to produce a set of derived fragment ions, and obtaining MS spectra on all or a subset of the derived fragment ions (MS″) spectra, and wherein the comparing further comprises sequentially comparing the MS″ spectra to bacterial LA and LTA MS″ spectra in the database to assist in identifying bacteria in the sample. This embodiment can be used, for example, where PMIS and/or MSE data is inconclusive, or where more detailed structural information on the relevant LA and/or LTA species is desirable. For example, this embodiment can be used to determine new LA and/or LTA structures. Thus, this embodiment can be used, for example, to identify new biomarkers of specific bacteria, as well as biomarkers of antibiotic resistant bacterial strains. Those of skill in the art will understand the types of mass spectrometry devices that are most suitably used with this embodiment of the invention. For example, an ion trap can be used to obtain full MS″ spectra, while other tandem mass spectrometers (ie: those with more than one mass analyzer, including but not limited to triple quad MS, QTOF MS, and Qtrap MS) can typically obtain $MS^3$ spectra.

As used herein, "derived fragment ions" are ions fragmented from the precursor ions; the first generation of such ions ($MS^2$) are fragmented from the $MS^1$ ions; the second generation of such derived fragment ions ($MS^3$) are fragmented from the $MS^2$ ions, etc. The process is iterative, with MS″ representing the number of generations. Thus, in one embodiment, the MS″ spectra data is obtained for at least two generations, $MS^1$ and $MS^2$, of derived fragment ions, and compared to bacterial LA and LTA $MS^1$ and $MS^2$ spectra in the database. In another embodiment, the MS″ spectra data is obtained for at least generations, $MS^1$, $MS^2$, and $MS^3$, of derived fragment ions, and compared to bacterial LA and LTA $MS^1$, $MS^2$, and $MS^3$ spectra in the database. The methods can be repeated to any desired "n" value of derived fragment ions (2, 3, 4, 5, 6, etc.) This embodiment is sequential, in that each successive generation of derived fragment ion derived from a single precursor ion can be compared against the database, in contrast to the MSE embodiment, where all subsequent generations of fragmented ions (or subsets thereof) are compared against the database simultaneously. For example, in one embodiment, $MS^1$ spectra are compared to the database and, if needed (ie: no difference seen, or not enough difference, etc.), $MS^2$ spectra are compared to the database. Similarly, $MS^3$ and further spectra can be obtained and compared to the database until a desired end-point is obtained (such as a difference seen either in chemical structure or relative abundance (from ion intensity values present in all spectra) of things all with the same structure). Each level of MS″ data reveals new structural details of LA and/or LTA that allows more refined structures to be defined.

In various embodiments, obtaining the MS″ MS spectra comprises obtaining MS″ MS spectra on 1, 2, 3, 4, 5, 6, 7, 8, 9, 10, 11, 12, 13, 14, 15, 16, 17, 18, 19, 20, 21, 22, 23, 24, or more MS″ ions; the number can differ from one generation of derived fragment ions to another, as deemed suitable for a given purpose. In one non-limiting example, the method comprises obtaining the $MS^n$ MS spectra for the 1, 2, 3, 4, 5, 6, 7, 8, 9, 10, 11, 12, 13, 14, 15, 16, 17, 18, 19, 20, 21, 22, 23, 24, or more most abundant $MS^n$ ions. In another embodiment, the method comprises obtaining the $MS^n$ MS spectra on all $MS^n$ ions.

The $MS^n$ MS spectra provides similar information on the $MS^n$ ions as did the PMIS on the precursor ions, including but not limited to information on (a) the m/z values of the $MS^n$ ions assessed; and (b) the relative abundance of the $MS^n$ ions generated. Similarly, the database to be used in this embodiment would further comprise previously obtained $MS^n$ MS spectra data similar to that present in the database for the PIMS spectra, including but not limited to $MS^n$ ion m/z values for LA or LTA molecules in the bacteria represented in the database. The data may also include the normalized, relative abundance of these $MS^n$ ions, as well as data regarding the MS technique used to generate the data.

Figure 11:
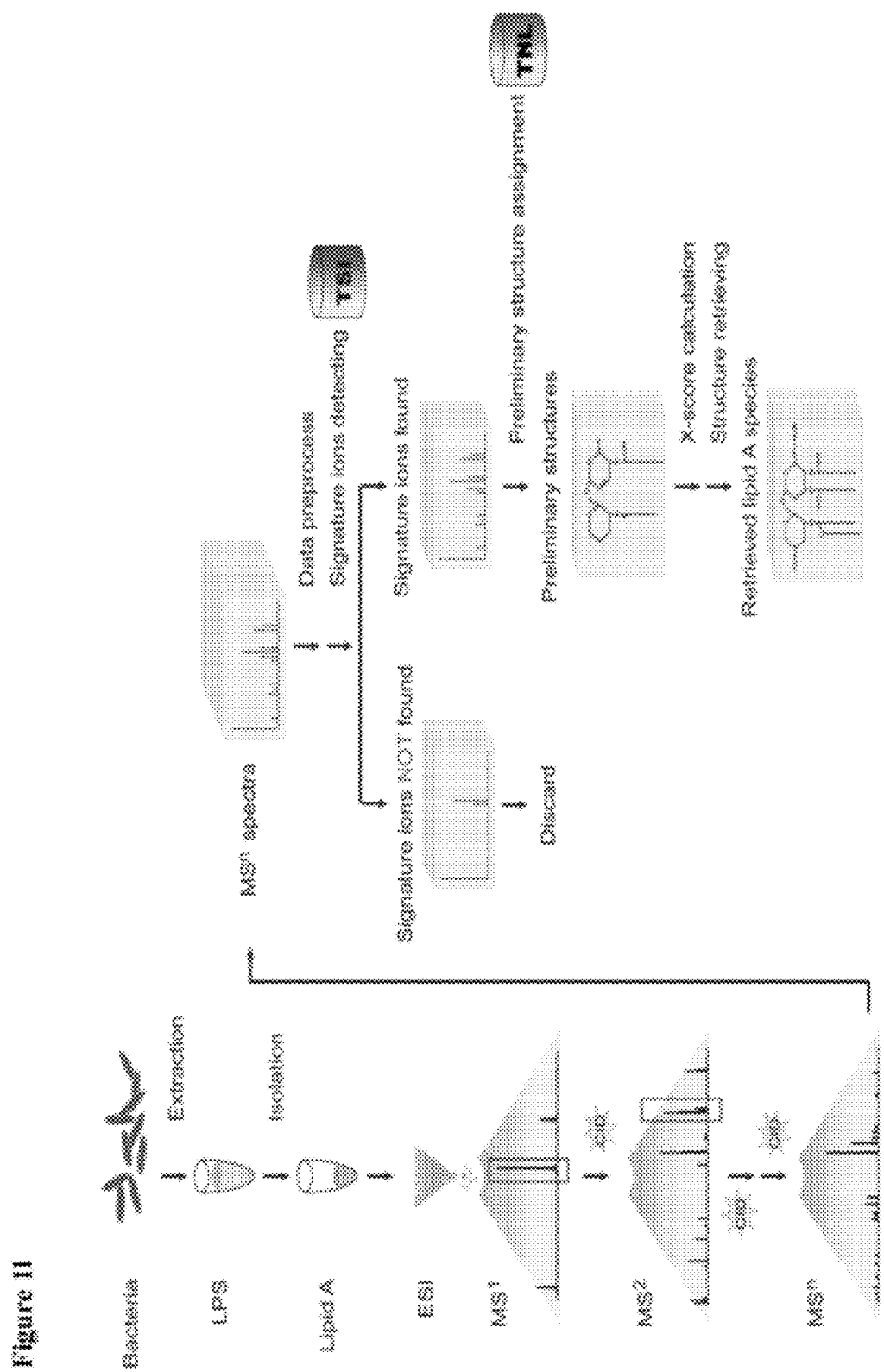
FIG. 11. Overview of HiTMS interpretation of lipid A hierarchical ESI-MS$^n$ data. Bacterial lipid A is isolated from LPS extraction and analyzed by ESI tandem mass spectrometry with hierarchical MS$^n$ strategy that acquires tandem mass spectra on each precursor ion and all of the derived fragment ions. The collection of MS$^n$ spectra is searched against the theoretical signature ion (TSI) database for observed signature ions. The neutral losses of signature ions in each spectrum are then searched against the theoretical neutral losses (TNL) database to identify dissociation formulae. Lipid A preliminary structures for each MS$^n$ spectral set are then proposed. Every assignment of preliminary structures is given a X-score based on the correlation between theoretical and acquired spectra. All candidate structures that pass the X-score cutoff are considered as accurate assignments.

In a further embodiment, that can be combined with any embodiment or combination of embodiments herein, the method further comprises searching the precursor ion and/or $MS^n$ spectra against a database of bacterial LA and LTA signature ions to identify signature ions in the precursor ion and/or $MS^n$ spectra. As used herein, "signature ions" are unique ions that help hypothesize the molecule's structure. In this embodiment, the database may comprise one database of previously identified signature ions for bacteria represented in the database, and a second database comprising the precursor ion and/or $MS^n$ ion MS spectra data. An exemplary embodiment is shown in FIG. 11. In this non-limiting example, bacterial LA is subjected to a hierarchical tandem mass spectrometry ($MS^n$) strategy that generates $MS^2$ and higher tandem mass spectra for each significant precursor ion detected in an $MS^1$ scan. Structures are assigned by the method which first searches a theoretical signature ion (TSI) database to detect signature ions and then confirms these by comparison to a database of expected theoretical neutral losses (TNL) from which a chemical formula and structure is derived.

Tandem mass spectrometry involves multiple steps of mass spectrometry selection, with some form of fragmentation occurring in between the stages. Exemplary tandem MS techniques suitable for use with the present claims include, but are not limited to, those disclosed in Shaffer et al. in the Journal of the American Society for Mass Spectrometry (JASMS), June 2007, Vol. 18, No. 6, pp. 1080-1092.

In a further embodiment, the comparing comprises (i) searching neutral losses of signature ions in the $MS^n$ spectra against a theoretical neutral loss database to identify dissociation formulae;

(ii) proposing LA and/or LTA candidate structures from bacteria in the sample based on the dissociation formulae and the signature ions in the $MS^n$ spectra;

(iii) assigning a score to each LA and/or LTA candidate structure based on correlation between theoretical and acquired $MS^n$ spectra, wherein candidate structures that meet or exceed a user-defined threshold are considered as accurate assignments.

As used herein, dissociation formulae are the pathway(s) of dissociation of a precursor ion.

In this embodiment, the database comprise, for example, a database based on the interpretation of LA and/or LTA fragmentation rules in tandem mass spectra which includes phosphate patterns as well as fatty acid and monosaccharide substituents. Direct bond cleavages of LA and/or LTA structures can be considered as the general template for fragmentation and structural inference. In a further embodiment, each database may comprise two sub-databases (or may comprise two separate but connected databases) for: (1) theoretical signature ions (TSI) and (2) theoretical neutral losses (TNL) (FIG. 11). For example, the observed LA signature ions can, be determined from the conserved characteristic of LA diglucosamine and named according to nomenclature known in the art. Based on the observed fragmentation templates of LA, signature ions can be calculated and compared to the theoretical signature ion (TSI) database. In a further embodiment, any MS spectra without any identifiable signature ions are discarded prior to comparing to the database.

To increase the structural diversity of LA and/or LTA represented in the TSI database, a user-defined carbon range of fatty acids can be applied (for example, 12:0 to 20:0 fatty acids). By systematically altering the fatty acid side chain lengths and positions, all possible signature ions can be computed, if desired, and incorporated into the TSI database. To facilitate structure assignment, neutral losses of signature ions can be calculated and put in the theoretical neutral loss (TNL) database. Additionally, common observed neutral losses that come from direct bond cleavages of LA other than cleavages of signature ions can also be included in the TNL database. Similarly, to increase the structural diversity covered by TNL databases, fatty acid compositions of TNL can be systematically altered within the user-defined carbon range.

Figure 12:
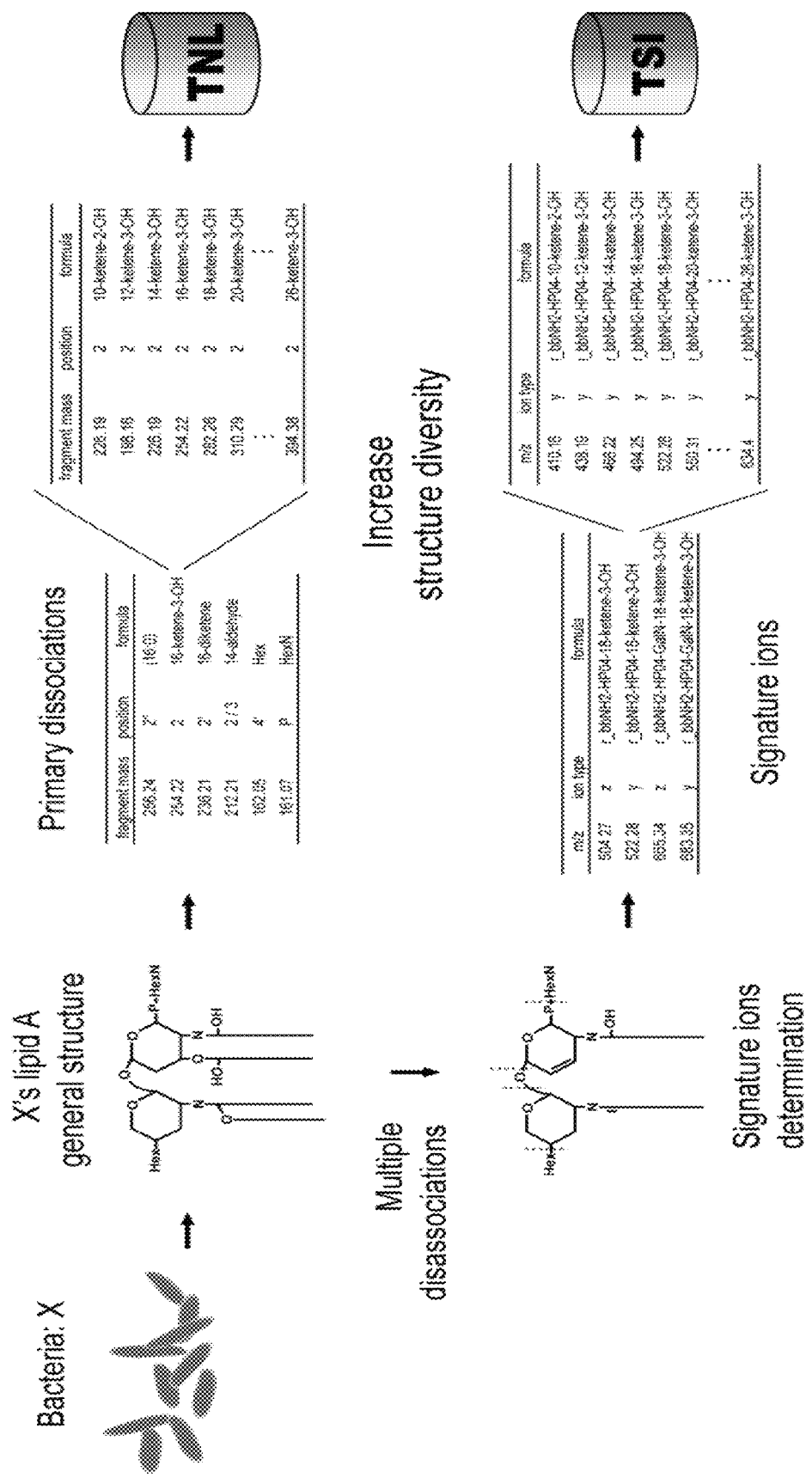
FIG. 12. Flowchart of the construction of theoretical databases. Lipid A general structure based on previous studies are used as a template for theoretical signature ion (TSI) and theoretical neutral loss (TNL) database construction. For the TNL database, fragment ion masses of primary dissociations are incorporated. The theoretical formula and masses of dissociations are calculated within a range of fatty acid lengths. Based on this logic, theoretical m/z values of signature ions are calculated and stored in the TSI database.
Figure 13:
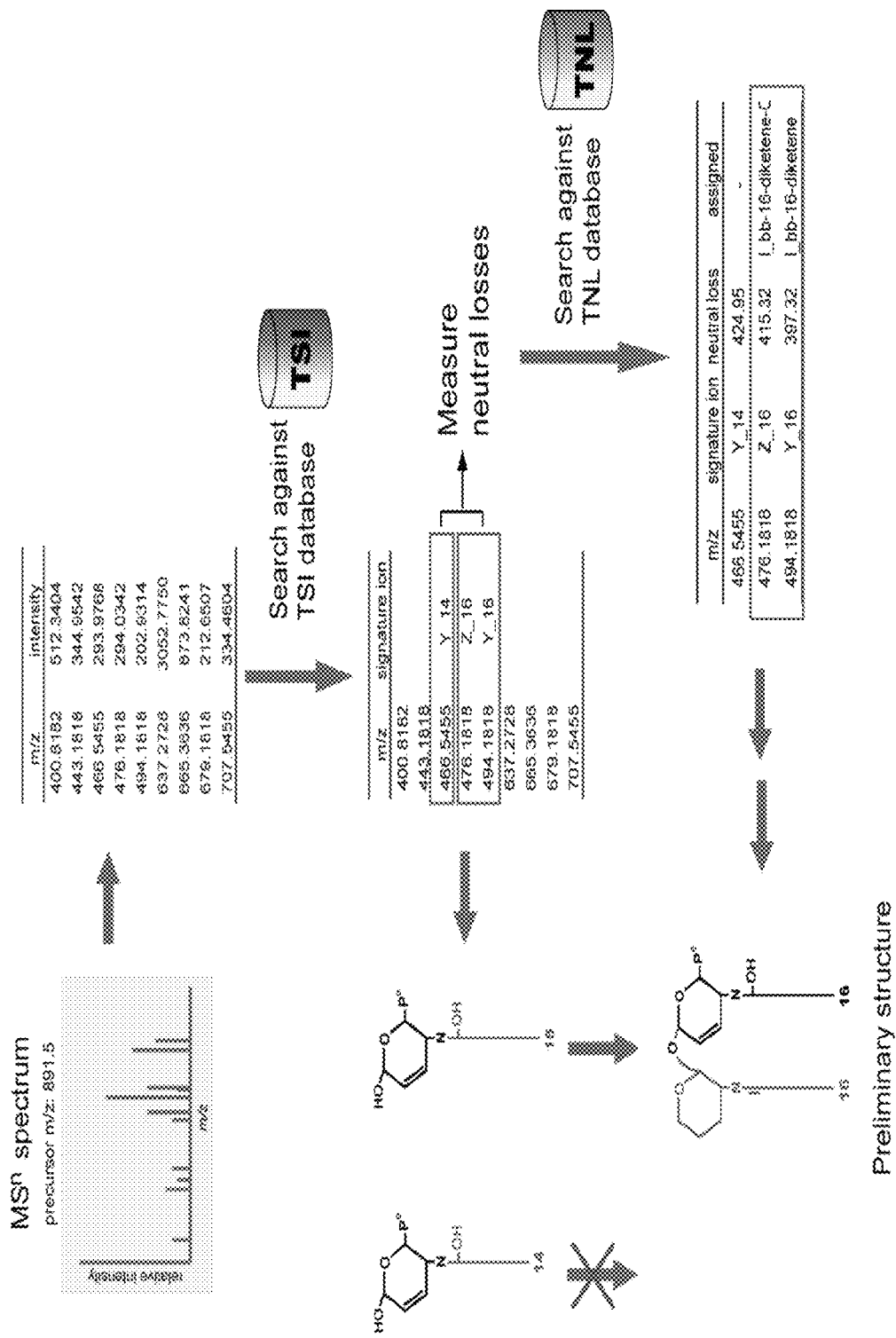
FIG. 13. Flowchart of preliminary candidate structural hypotheses. A peak list is extracted from MS$^n$ spectra by MassSpecWavelet peak detection algorithm. The extracted m/z peaks are searched against the theoretical signature ion (TSI) database for signature ions, which suggest the formulae of the reducing end of lipid A. Neutral losses of all possible ion indicators are measured and searched against the theoretical neutral losses (TNL) database. Identified neutral losses provide information on the remaining structures. Preliminary structures are then proposed by combining the complementary portions.

In this embodiment, acquired $MS^n$ spectra can be searched against the TSI database to find possible signature ions and spectra without any identifiable signature ions can be discarded (FIGS. 11-13). Any identified signature ions suggest formulae corresponding to the reducing and/or non-reducing portions of LA. By subtracting the mass of signature ions from their precursors, the neutral losses of signature ions can be subsequently calculated and searched against the TNL database. The combination of signature ions and matched neutral losses may be used to provide a preliminary candidate structure (FIGS. 11-13).

In a further embodiment, searching neutral losses of signature ions in the $MS^n$ spectra against a theoretical neutral loss database to identify dissociation formulae comprises (A) determining a neutral loss of every $MS^n$ spectrum's precursor ion in the corresponding $MS^{n-1}$ spectrum and searching against the theoretical neutral loss database; and (B) iteratively repeating step (A) until level $MS^1$ is reached; and wherein step (ii) comprises proposing the LA and/or the LTA structures from the bacteria in the sample based on the integrating data from each $MS^n$ level.

In this embodiment, the calculated neutral losses of all the ions in each spectrum can also searched against the TNL database to provide desired information for spectrum annotation (ie: a lipid-spectrum match (LSM). After preliminary structures are assigned, neutral loss of one or more (or every) $MS^n$ spectrum's precursor ion can be calculated in the corresponding $MS^{n-1}$ spectrum and searched against the TNL database again to, for example, identify the possible dissociation patterns. The method may proceed iteratively until the $MS^1$ level is reached. The final structures can be deduced, for example, by integrating the information gained from the different levels of $MS^n$ data.

In another embodiment, assigning a score to each LA and/or LTA candidate structure based on correlation between theoretical and acquired $MS^n$ spectra comprises (A) fragmenting the LA and/or the LTA candidate structures by direct bond cleavage to produce fragmentations;

(B) combining the fragmentations into a reconstructed mass spectra representing the theoretical dissociation of the LA and/or the LTA candidate structures; and (C) assigning the score to each of the LA and/or the LTA candidate structure based on correlation between theoretical $MS^n$ spectra and the reconstructed mass spectra.

In this embodiment, for every LSM, a hypothetical LA structure can be fragmented in silico based primarily on direct bond cleavages, including glycosidic bond cleavages (i.e. A/X, B/Y, C/Z type ions), losses of O- and N-linked acyl chains, losses of phosphate, losses of monosaccharide and perturbations representing combined losses. Fragmentations can, for example, then be combined into a reconstructed mass spectrum representing the theoretical dissociation of the candidate structure.

In another embodiment, an X-score may be applied to a lipid-spectrum match (LSM) to evaluate the closeness of fit between one or more acquired $MS^n$ spectrum and a theoretical tandem mass spectrum. The peak intensity of each reconstructed mass spectrum can, for example, be assigned a Boolean value where 1 represents, for example, the existence of a fragmentation of such m/z value. The X-score between the acquired mass spectrum and the reconstructed mass spectrum of hypothetical structure can be measured using any suitable scoring scheme, including but not limited to those disclosed in the examples below.

In one embodiment, each X-score calculation is a scalar dot product between reconstructed mass spectrum x and the pre-processed acquired mass spectrum y' with τ is the correction factor.

In a further embodiment, the methods may comprise use of a target-decoy strategy, for example, generating decoys by shuffling the candidate LA and/or LTA structures on-the-fly while analyzing each $MS^n$ spectrum. In one embodiment, such shuffling only occurs on the position and length of LA and/or LTA fatty acid side chains. This approach ensures that every decoy LA and/or LTA exhibits precisely the same molecular composition and mass as the target (i.e. candidate) LA and/or LTA structures. X-score of both candidate and decoy LSM can then be calculated to help evaluate the significance.

The methods of any embodiment or combination of embodiments of the invention can be used alone, or in combination with other bacterial identification methods, such as those based on protein MS patterns. Thus, in another embodiment, the methods comprise obtaining mass spectrometry (MS) spectra on precursor ions for bacterial proteins in the sample; comparing the protein MS spectra to a database of bacterial protein precursor ion mass spectrometry spectra; wherein the comparing is used to help identify bacteria in the sample. In a further embodiment, the sample is processed to obtain LA and/or LTA together with protein using a standard protocol that maintains the pH of the sample between about 4 to 5, such as a pH of about 4.5, for the portion of the sample processing for LA and/or LTA isolation. In one exemplary embodiment, such a technique would comprise contacting a bacterial pellet with sodium acetate (such as 5-20 ml), or any other suitable treatment resulting in a sample pH of about 4.5 with or without heating, and mixing to resuspend the bacteria. Next, acetonitrole is added (such as about 5-20 ml) and the sample mixed, followed by centrifugation (such as at about 25,000 g for about 2 minutes) to obtain the supernatant for MS analysis. In another embodiment, the bacterial sample is split into two samples, with a first sample pelleted and treated as above, and a second sample treated similarly, except that the sodium acetate is replaced with formic acid. In this embodiment, the first sample can be used for LA and/or LTA analysis and the second sample can be used for protein analysis. In a further embodiment, the sample is treated via the sodium acetate procedure and a portion of the sample is used for LA and/or LTA analysis, and the rest of the sample is treated with formic acid for protein analysis.

In this embodiment, the methods of the present invention can be used in combination with protein MS analysis to, for example, improve the efficiency of the protein MS analysis. One embodiment of such protein MS analysis is the Bruker MALDI Biotyper™ mass spectrometer platform (Bruker Daltonics) See, for example, Sauer et al., PLoS ONE 3(7): e2843. doi:10.1371/journal.pone.0002843. The methods of the present invention provide improved accuracy in bacterial identification compared to protein-based MS techniques (or in combination with protein-based MS techniques), as indicated by the following examples (See, for example, FIG. 6 for results using current methods):

(a) *Shigella* is considered as a part of the *E. coli* species phylogenetically, and gives no different pattern in protein-based MS, while it can be distinguished from *E. coli* using the methods of the present invention.

(b) *Streptococcus pneumoniae* identification requires a second protein-MS based test for confirmation (gold standard MLST). As *S. pneumoniae* is very closely related to the S. mitis group, there might occur misidentifications, mostly with low ID scores. 16S rDNA sequencing also is not sufficient for differentiation of *Streptococcus pneumoniae* and *S. mitis*, while the methods of the present invention can distinguish *Streptococcus pneumoniae* and *S. mitis*.

(c) Three *Pseudomonas* species are very closely related to *Stenotrophomonas maltophila* and accordingly may appear as "mis"identification results using protein-based MS analysis: *Ps. hibiscola, Ps. geniculata*, and *Ps. beteli*. Furthermore, the former subspecies *S. maltophila africana*, now *S. africana*, is not securely distinguishable by the MALDI Biotyper™

(d) *Acinetobacter baumanii-calcoaceticus* complex (*A. baumanii, A. calcoaceticus, A. genospecies* 3, *A. genospecies* 13): Species differentiation can be difficult using protein-based MS techniques. While *A. baumanii* and *A. calcoaceticus* can be differentiated well, there are several members of the "Genospecies 3" clustering with *A. baumanii* or *A. calcoacteticus*, which can lead to "*A. genospecies* 3" ID result where biochemistry will identify *A. baumanii* or *A. calcoaceticus*. The methods of the present invention may be used for accurate species distinction within the *Acinetobacter baumanii-calcoaceticus* complex.

(e) *Enterobacter cloacae* complex is a group of six very closely related species with a similar resistance pattern: *Enterobacter asburiae, Enterobacter cloacae, Enterobacter hormaechei, Enterobacter kobei, Enterobacter ludwigii*, and *Enterobacter nimipressuralis*. Distinguishing between species within the *Enterobacter cloacae* complex is not possible using protein-based MS techniques.

(f) The *Pseudomonas putida* group is very diverse and differentiation within the group is limited using protein-based MS techniques, while the methods of the present invention can be used to distinguish between members of the group.

(g) *Bordetella pertussis* and *Bordetella bronchioseptica* are closely related and show very similar protein MS patterns; the methods of the present invention can be used to help distinguish *Bordetella pertussis* and *Bordetella bronchioseptica*.

(h) *Achromobacter xylosoxidans* and *Achromobacter ruhlandii* protein-based MS patterns are very similar; the methods of the present invention can be used to help distinguish *Achromobacter xylosoxidans* and *Achromobacter ruhlandii*.

(i) *Pseudomonas fluorescens* is a member of a very diverse group that that cannot be distinguished using protein-based MS methods (any hits in this group are considered as "*Pseudomonas fluorescens* group"). The methods of the present invention can be used to help distinguish between different members of the *Pseudomonas fluorescens* group.

(j) *Burkholderia cepacia* complex can be separated well from other *Burkholderia* species, but sub-species resolution within *Burkholderia cepacia* complex is currently limited using protein-based MS techniques. The methods of the present invention can be used to help distinguish between different members of the *Burkholderia cepacia* complex.

(k) *Bacteroides nordii* and *Bacteroides salyersiae* are very closely related and are not reliably distinguished using the MALDI Biotyper™. The methods of the present invention can be used to help distinguish between *Bacteroides nordii* and *Bacteroides salyersiae*.

(l) *Listeria* species are very closely related, and only *Listeria greyi* can be differentiated reliably from the other *Listeria* species using protein-based MS techniques. The methods of the present invention can be used to help distinguish between different *Listeria* species.

(m) *Candida africana* is a subspecies of *Candida albicans*, and the two cannot be distinguished using protein-based MS analysis. The methods of the present invention can be used to help distinguish between *Candida africana* and *Candida albicans*.

(n) Some species within the genus *Aeromonas* are very closely related, leading to a very similar pattern using protein-based MS analysis. The methods of the present invention can be used to help distinguish between species within the genus *Aeromonas*.

(O) *Klebsialla oxytoca* and *Raoutella ornitholytica* are very similar in protein-based MS patterns, while the methods of the present invention can be used to help distinguish between *Klebsialla oxytoca* and *Raoutella ornitholytica*.

Example Computing Environment

Results of a comparison between one or more input spectra generated by a mass spectrometer or similar device (e.g., PIMS, $MS^E$, $MS^n$ spectra) and one or more stored spectra (e.g., spectra stored as in a database) can be carried out in an automated fashion using a computing device acting as a "spectra identifier."

Upon completion, content related the results of the comparison can be generated by the spectra identifier. For example, the content can include graphs, images, alphanumeric, and/or video content preferably displayed to a user via a graphical user interface on either the spectra identifier or a client device.

For example, FIG. 1 shows spectra identifier 108 configured to communicate, via network 106, with mass spectrometer 102 and client devices 104a, 104b. Network 106 may correspond to a LAN, a wide area network (WAN), a corporate intranet, the public Internet, or any other type of network configured to provide a communications path between networked computing devices. The network 106 may also correspond to a combination of one or more LANs, WANs, corporate intranets, and/or the public Internet.

Although FIG. 1 only shows two client devices, distributed application architectures may serve tens, hundreds, or thousands of client devices. Moreover, client devices 104a and 104b (or any additional client devices) may be any sort of computing device, such as an ordinary laptop computer, desktop computer, network terminal, wireless communication device (e.g., a cell phone or smart phone), and so on. In some embodiments, client devices 104a and 104b can be dedicated to MS and/or bacteriological research. In other embodiments, client devices 104a and 104b can be used as general purpose computers that are configured to perform a number of tasks and need not be dedicated to MS or bacteriological research. In still other embodiments, the functionality of spectra identifier 108 and/or spectra database 110 can be incorporated in a client device, such as client devices 104a and/or 104b. In even other embodiments, the functionality of spectra identifier 108 and/or spectra database 110 can be incorporated into mass spectrometer 102.

Mass spectrometer 102 can be configured to receive an input material e.g., LA and/or LTA, and generate one or more spectra as output. For example, mass spectrometer 102 can be an electrospray ionization (ESI) tandem mass spectrometer or a SAWN-based mass spectrometer. In some embodiments, the output spectra can be provided to another device; e.g., spectra identifier 108 and/or spectra database 110, perhaps to be used as an input to the device. In other embodiments, the output spectra can be displayed on mass spectrometer 102, client devices 104a and/or 104b, and/or spectra identifier 108.

Spectra identifier 108 can be configured to receive, as an input, one or more spectra from mass spectrometer 102 and/or client device(s) 104a and/or 104b via network 106. In some embodiments, spectra identifier can be configured to directly receive input spectra via keystroke, touchpad or similar data input to spectra identifier 108, hard-wired connection(s) to mass spectrometer 102 and/or client device(s) 104a and/or 104(b), accessing storage media configured to store input spectra (e.g., spectra database 110, flash media, compact disc, floppy disk, magnetic tape), and/or any other technique to directly provide input spectra to spectra identifier 108.

The one or more input spectra can include, for example, a $MS^n$ sequence of n related spectra from a given input material. Each of the n related spectra can relate to one or more different ions and/or neutral fragments of the input material.

Spectra identifier 108 can be configured to generate results of spectra identification by comparing one or more input spectra to stored spectra 112. For example, stored spectra 112 can be known precursor ion mass spectrometry spectra, $MS^E$ ion mass spectrometry spectra, or $MS^n$. As shown in FIG. 1, stored spectra 112 can reside in spectra database 110. When performing spectra identification, spectra identifier 108 can access and/or query spectra database 110 to retrieve part or all of stored spectra 112. In some embodiments, spectra identifier 108 can perform the comparison task directly; while in other embodiments, part or all of the spectra identification task can be performed by spectra database 110, perhaps by executing one or more query language commands upon stored spectra 112.

While FIG. 1 shows spectra identifier 108 and spectra database 110 directly connected, in other embodiments, spectra identifier 108 can include the functionality of spectra database 110, including storing stored spectra 112. In still other embodiments, spectra identifier 108 and spectra database 110 can be connected via network 106.

Upon identifying the input spectra, spectra identifier 108 can be configured to provide content at least related to results of spectra identification, as requested by client devices 104a and/or 104b. The content related to results of spectra identification can include, but is not limited to, web pages, hypertext, scripts, binary data such as compiled software, images, audio, and/or video. The content can include compressed and/or uncompressed content. The content can be encrypted and/or unencrypted. Other types of content are possible as well.

Computing Device Architecture

Figure 2A:
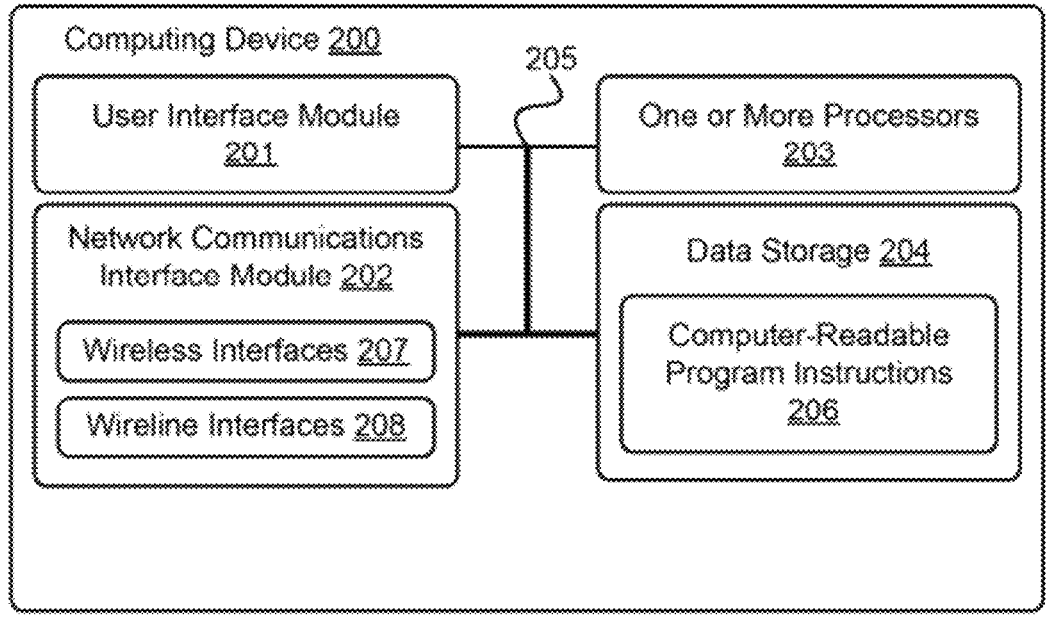
FIG. 2A is a block diagram of a computing device (e.g., system) in accordance with an example embodiment.

FIG. 2A is a block diagram of a computing device (e.g., system) in accordance with an example embodiment. In particular, computing device 200 shown in FIG. 2A can be configured to perform one or more functions of mass spectrometer 102, client device 104a, 104b, network 106, spectra identifier 108, spectra database 110, and/or stored spectra 112. Computing device 200 may include a user interface module 201, a network-communication interface module 202, one or more processors 203, and data storage 204, all of which may be linked together via a system bus, network, or other connection mechanism 205.

User interface module 201 can be operable to send data to and/or receive data from external user input/output devices. For example, user interface module 201 can be configured to send and/or receive data to and/or from user input devices such as a keyboard, a keypad, a touch screen, a computer mouse, a track ball, a joystick, a camera, a voice recognition module, and/or other similar devices. User interface module 201 can also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, either now known or later developed. User interface module 201 can also be configured to generate audible output(s), such as a speaker, speaker jack, audio output port, audio output device, earphones, and/or other similar devices.

Network-communications interface module 202 can include one or more wireless interfaces 207 and/or one or more wireline interfaces 208 that are configurable to communicate via a network, such as network 106 shown in FIG. 1. Wireless interfaces 207 can include one or more wireless transmitters, receivers, and/or transceivers, such as a Bluetooth transceiver, a Zigbee transceiver, a Wi-Fi transceiver, a WiMAX transceiver, and/or other similar type of wireless transceiver configurable to communicate via a wireless network. Wireline interfaces 208 can include one or more wireline transmitters, receivers, and/or transceivers, such as an Ethernet transceiver, a Universal Serial Bus (USB) transceiver, or similar transceiver configurable to communicate via a twisted pair, one or more wires, a coaxial cable, a fiber-optic link, or a similar physical connection to a wireline network.

In some embodiments, network communications interface module 202 can be configured to provide reliable, secured, and/or authenticated communications. For each communication described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as CRC and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well or in addition to those listed herein to secure (and then decrypt/decode) communications.

Processors 203 can include one or more general purpose processors and/or one or more special purpose processors (e.g., digital signal processors, application specific integrated circuits, etc.). Processors 203 can be configured to execute computer-readable program instructions 206 contained in storage 204 and/or other instructions as described herein.

Data storage 204 can include one or more computer-readable storage media that can be read and/or accessed by at least one of processors 203. The one or more computer-readable storage media can include volatile and/or non-volatile storage components, such as optical, magnetic, organic or other memory or disc storage, which can be integrated in whole or in part with at least one of processors 203. In some embodiments, data storage 204 can be implemented using a single physical device (e.g., one optical, magnetic, organic or other memory or disc storage unit), while in other embodiments, data storage 204 can be implemented using two or more physical devices.

Data storage 204 can include computer-readable program instructions 206 and perhaps additional data. For example, in some embodiments, data storage 204 can store part or all of a spectra database and/or stored spectra, such as spectra database 110 and/or stored spectra 112, respectively. In some embodiments, data storage 204 can additionally include storage required to perform at least part of the herein-described methods and techniques and/or at least part of the functionality of the herein-described devices and networks.

Figure 2B:
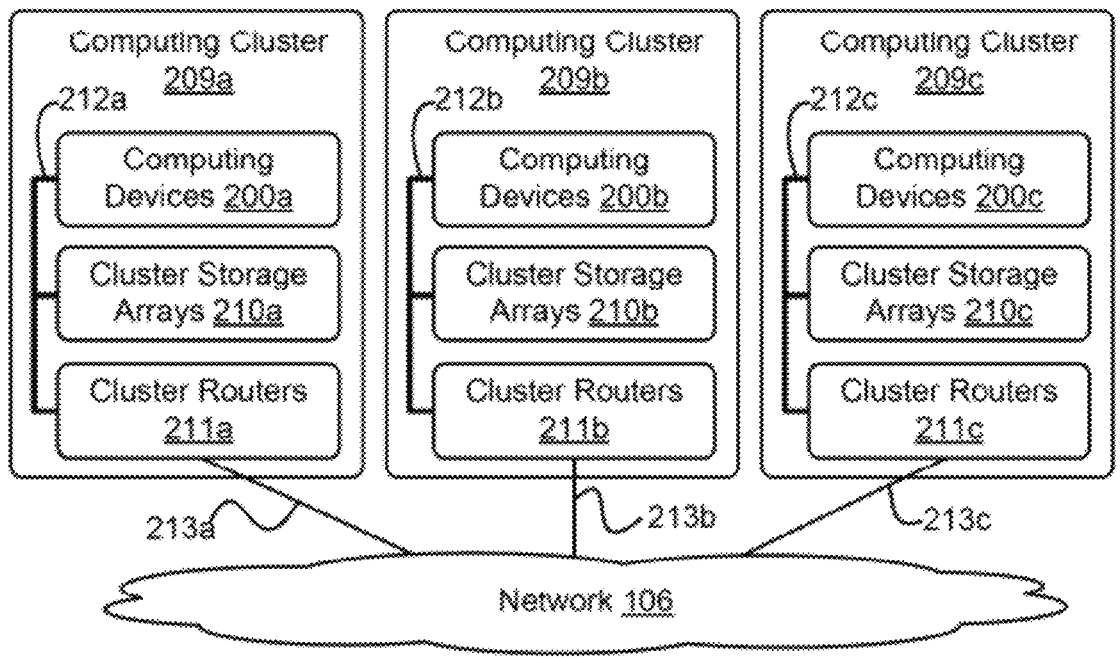
FIG. 2B depicts a network 106 of computing clusters 209a, 209b, and 209c arranged as a cloud-based server system in accordance with an example embodiment.

FIG. 2B depicts a network 106 of computing clusters 209a, 209b, 209c arranged as a cloud-based server system in accordance with an example embodiment. Spectra identifier 108 and/or spectra database 110 can be cloud-based devices that store program logic and/or data of cloud-based applications and/or services. In some embodiments, spectra identifier 108 and spectra database 110 can be a single computing device residing in a single computing center. In other embodiments, spectra identifier 108 and/or spectra database 110 can include multiple computing devices in a single computing center, or even multiple computing devices located in multiple computing centers located in diverse geographic locations. For example, FIG. 1 depicts each of spectra identifier 108 and spectra database 110 residing in different physical locations.

In some embodiments, data and services at spectra identifier 108 and spectra database 110 can be encoded as computer readable information stored in tangible computer readable media (or computer readable storage media) and accessible by client devices 104a and 104b, and/or other computing devices. In some embodiments, data at spectra identifier 108 and/or spectra database 110 can be stored on a single disk drive or other tangible storage media, or can be implemented on multiple disk drives or other tangible storage media located at one or more diverse geographic locations.

FIG. 2B depicts a cloud-based server system in accordance with an example embodiment. In FIG. 2B, the functions of spectra identifier 108 and/or spectra database 110 can be distributed among three computing clusters 209a, 209b, and 208c. Computing cluster 209a can include one or more computing devices 200a, cluster storage arrays 210a, and cluster routers 211a connected by a local cluster network 212a. Similarly, computing cluster 209b can include one or more computing devices 200b, cluster storage arrays 210b, and cluster routers 211b connected by a local cluster network 212b. Likewise, computing cluster 209c can include one or more computing devices 200c, cluster storage arrays 210c, and cluster routers 211c connected by a local cluster network 212c.

In some embodiments, each of the computing clusters 209a, 209b, and 209c can have an equal number of computing devices, an equal number of cluster storage arrays, and an equal number of cluster routers. In other embodiments, however, each computing cluster can have different numbers of computing devices, different numbers of cluster storage arrays, and different numbers of cluster routers. The number of computing devices, cluster storage arrays, and cluster routers in each computing cluster can depend on the computing task or tasks assigned to each computing cluster.

In computing cluster 209a, for example, computing devices 200a can be configured to perform various computing tasks of spectra identifier 108. In one embodiment, the various functionalities of spectra identifier 108 can be distributed among one or more of computing devices 200a, 200b, and 200c. Computing devices 200b and 200c in computing clusters 209b and 209c can be configured similarly to computing devices 200a in computing cluster 209a. On the other hand, in some embodiments, computing devices 200a, 200b, and 200c can be configured to perform different functions.

In some embodiments, computing tasks and stored data associated with server devices 108 and/or 110 can be distributed across computing devices 200a, 200b, and 200c based at least in part on the processing requirements of spectra identifier 108 and/or spectra database 110, the processing capabilities of computing devices 200a, 200b, and 200c, the latency of the network links between the computing devices in each computing cluster and between the computing clusters themselves, and/or other factors that can contribute to the cost, speed, fault-tolerance, resiliency, efficiency, and/or other design goals of the overall system architecture.

The cluster storage arrays 210a, 210b, and 210c of the computing clusters 209a, 209b, and 209c can be data storage arrays that include disk array controllers configured to manage read and write access to groups of hard disk drives. The disk array controllers, alone or in conjunction with their respective computing devices, can also be configured to manage backup or redundant copies of the data stored in the cluster storage arrays to protect against disk drive or other cluster storage array failures and/or network failures that prevent one or more computing devices from accessing one or more cluster storage arrays.

Similar to the manner in which the functions of spectra identifier 108 and/or spectra database 110 can be distributed across computing devices 200a, 200b, and 200c of computing clusters 209a, 209b, and 209c, various active portions and/or backup portions of these components can be distributed across cluster storage arrays 210a, 210b, and 210c. For example, some cluster storage arrays can be configured to store the data of spectra identifier 108, while other cluster storage arrays can store data of spectra database 110. Additionally, some cluster storage arrays can be configured to store backup versions of data stored in other cluster storage arrays.

The cluster routers 211a, 211b, and 211c in computing clusters 209a, 209b, and 209c can include networking equipment configured to provide internal and external communications for the computing clusters. For example, the cluster routers 211a in computing cluster 209a can include one or more internet switching and routing devices configured to provide (i) local area network communications between the computing devices 200a and the cluster storage arrays 201a via the local cluster network 212a, and (ii) wide area network communications between the computing cluster 209a and the computing clusters 209b and 209c via the wide area network connection 213a to network 106. Cluster routers 211b and 211c can include network equipment similar to the cluster routers 211a, and cluster routers 211b and 211c can perform similar networking functions for computing clusters 209b and 209b that cluster routers 211a perform for computing cluster 209a.

In some embodiments, the configuration of the cluster routers 211a, 211b, and 211c can be based at least in part on the data communication requirements of the computing devices and cluster storage arrays, the data communications capabilities of the network equipment in the cluster routers 211a, 211b, and 211c, the latency and throughput of local networks 212a, 212b, 212c, the latency, throughput, and cost of wide area network links 213a, 213b, and 213c, and/or other factors that can contribute to the cost, speed, fault-tolerance, resiliency, efficiency and/or other design goals of the moderation system architecture.

Example Spectrum Identification Algorithm

Figure 3A:
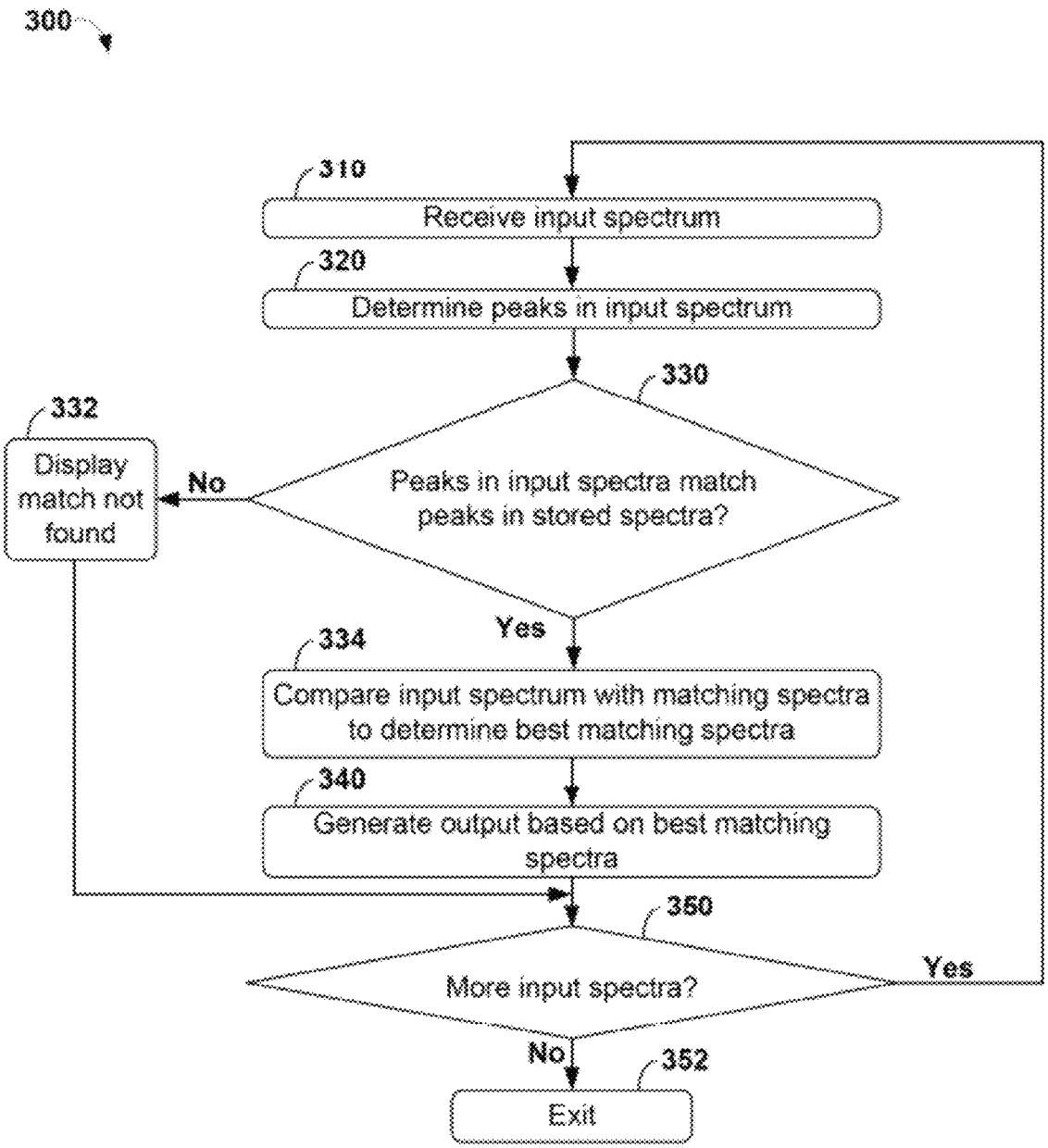
FIG. 3A shows an example method 300 for spectral identification. At block 310, an input spectrum is received.

FIG. 3A shows an example method 300 for spectral identification. At block 310, an input spectrum is received. The input spectrum can utilize any format for a spectrum, such as but not limited to utilizing a raw data format, JCAMP-DX, ANDI-MS, mzXML, mzData, and/or mzML. Other formats can be used as well or instead.

At block 320, one or more peaks in the input spectrum are identified. The peaks can be determined using the MassSpecWavelet techniques discussed above or via other techniques, such sorting the input spectrum by relative intensity or abundance and taking the top T, T>0, points in the sorted input spectrum. Other techniques can be used as well.

Figure 3B:
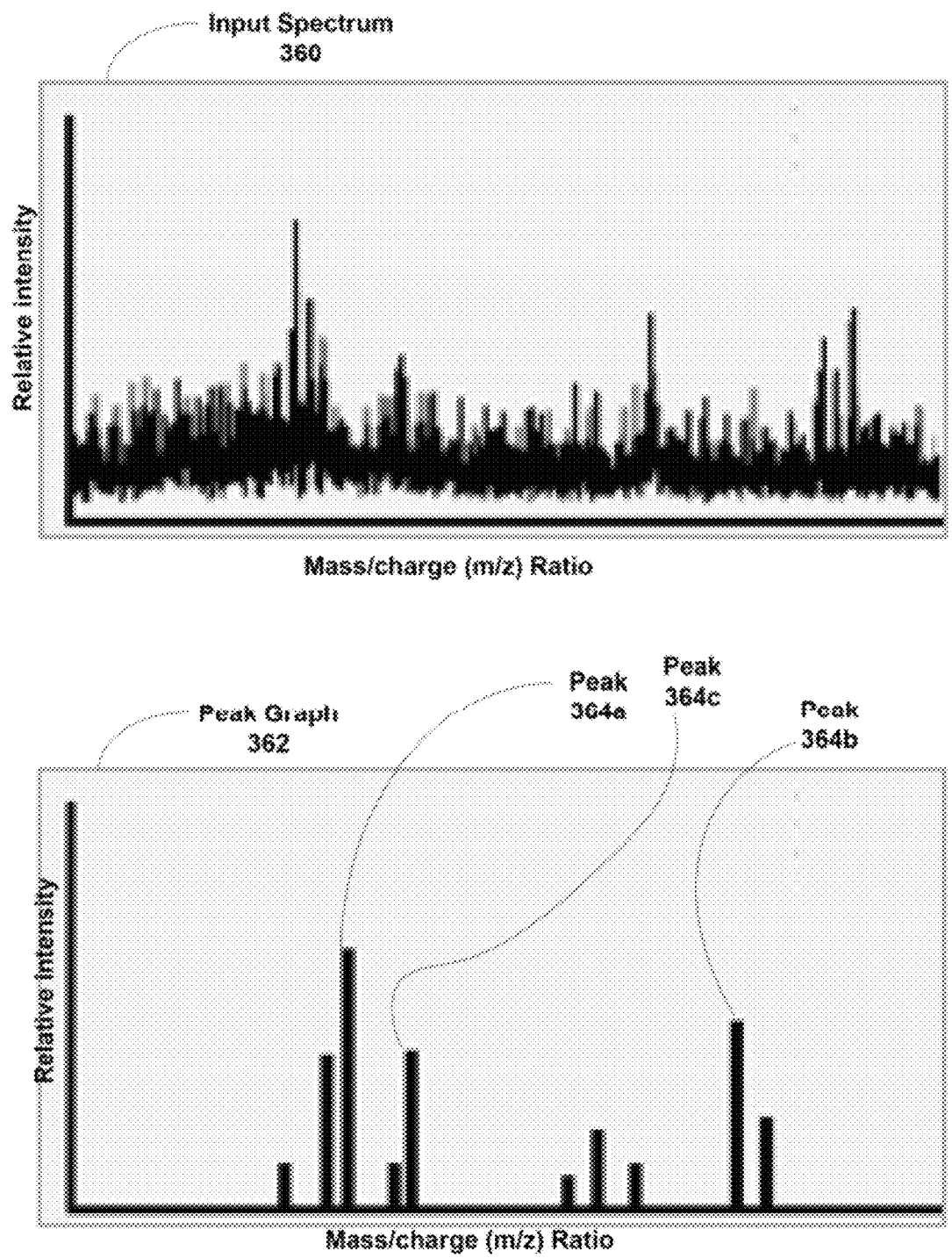
FIG. 3B shows and example input spectrum 360 and corresponding graph 362 of peaks of input spectrum 360.

FIG. 3B shows and example input spectrum 360 and corresponding graph 362 of peaks of input spectrum 360. FIG. 3B specifically identifies the three highest peaks, respectively peaks 364a, 364b, and 364c, in input spectrum 360 as displayed in peak graph 362.

Returning to FIG. 3A, at block 330, a comparison between peaks of the input spectra and peaks in one or more stored spectra is performed. The stored spectra can be stored in any format for a spectrum, such as but not limited to storage in a raw data format, JCAMP-DX, ANDI-MS, mzXML, mzData, and/or mzML. In some embodiments, the input spectrum and/or some or all of the stored spectra can be converted between formats before or during the comparison. The stored spectra can also include additional information, such as a name of a compound, molecule, structure, substance, ion, fragment, or other identifier that can be used to identify the spectrum. For example, if a stored spectrum is a spectrum for pure water, then the stored spectrum can have additional information such as "water" or "$H_2O$" to help identify the stored spectrum.

If the peaks of the input spectra match peaks in one or more stored spectra, method 300 proceeds to block 334. Otherwise, method 300 proceeds to block 332 where a "no match" display is generated and displayed. After completing the procedures of block 332, method 300 can proceed to block 350.

At block 334, the input spectrum is compared to each of the one or more matching and stored spectra identified at block 330. For example, consider spectra provided with relative intensity and mass/charge ratio values. For each of the input spectrum and the matching spectra, a dot product of the relative abundance and mass/charge value can be taken to determine a weighted average mass/charge value. Then, the weighted average mass/charge value for the input spectrum $A(IS)$ can be compared to each of the weighted average mass/charge values for the matching spectra $A(MS_i)$, where i=1 to the number of matching spectra. The matching spectra j with the closest weighted average mass/charge value $A(MS_j)$, to $A(IS)$ can be considered to be a best matching spectrum. In some embodiments, a difference between $A(MS_j)$ and $A(IS)$ can be determined, and if the absolute value of this difference is greater than a threshold, then the best matching spectrum can be considered not to match the input spectrum. If the two spectra are not considered to match, method 300 can proceed to block 332 (transfer of control not shown in FIG. 3A).

At block 340, when a match is found, an output based on the best matching spectrum can be generated. For example, if identifying information for the stored spectrum is maintained, the output can indicate an identity of the matching spectrum. Also or instead, the input spectrum and/or the matching spectrum can be shown as part of the display. Further, the A(MS$_j$) and A(IS) can be part of the display as well. Other information can be part of the display as well.

The output can be provided using some or all components of a user interface module, such as user interface module 201, and/or a network communications interface module, such as network communication interface module 202. For example, the output can be displayed on a display, printed, emitted as sound using one or more speakers, and/or transmitted to another device using network communications interface module. Other examples are possible as well.

At block 350, a determination is made as to whether there are additional input spectra to be processed. If there are additional spectra to be processed, method 300 can proceed to block 310; otherwise, method 300 can proceed to block 352, where method 300 exits.

Figure 4:
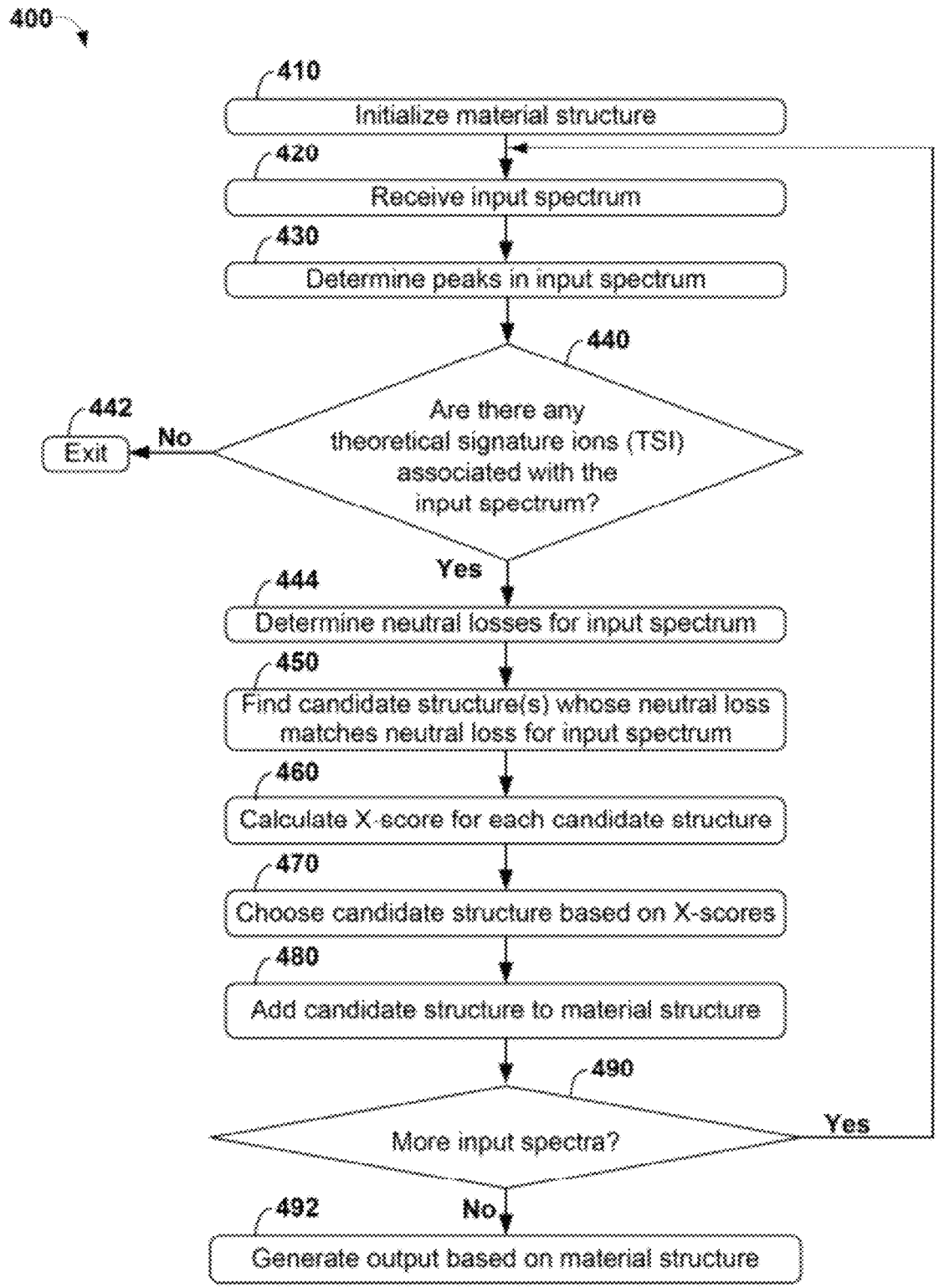
FIG. 4 shows another example method 400 for spectral identification.

FIG. 4 shows another example method 400 for spectral identification.

At block 410 of method 400, a material structure is initialized. For example, the material structure can be initialized to no structure, or, if a material in a known class of materials (e.g., lipids) are to be analyzed, the material structure can be initialized to a generic member of the known class of materials.

At block 420, an input spectrum is received. The input spectrum can be expressed in any format for a spectrum, such as but not limited to raw data format, JCAMP-DX, ANDI-MS, mzXML, mzData, or mzML. Other formats can be used as well or instead.

At block 430, one or more peaks in the input spectrum are identified. The peaks can be determined using the MassSpec-Wavelet techniques discussed above or via other techniques, such sorting the input spectrum by relative intensity or abundance and taking the top T, T>0, points in the sorted input spectrum. Other techniques can be used as well.

At block 440, a determination is made as to whether there are any theoretical signature ions (TSIs) associated with the input spectrum. The determination can be made via a database query or other comparison between stored data for theoretical signature ions and the identified peaks of the input spectrum. In some embodiments, data about one or more precursor ions can be stored and associated with a theoretical signature ion. In other embodiments, probability information, such as a classification score for identification, can be generated, passed in to the database as part of the database query, and used to aid identification of a theoretical signature ion.

If one or more theoretical signature ions are found to be associated with the input spectrum, then method 400 can proceed to block 444.

However, if no theoretical signature ions are found to be associated with the input spectrum, then method 400 can proceed to block 442 and exit.

At block 444, neutral losses for the input spectrum can be determined. For example, a mass of a signature ion can be calculated and used as the value of the neutral loss of the input spectrum. If multiple signature ions are determined to be associated with the input spectrum, the mass of each signature ion can be used as a neutral loss value. As another example, the stored data for the signature ion can include one or more neutral loss values, which can be used as the neutral loss value(s) for the input spectrum.

At block 450, candidate structures(s) can be found whose neutral loss matches a neutral loss for the input spectrum. For example, one or more theoretical neutral loss (TNL) values can be stored in a theoretical neutral loss database. In some embodiments, the theoretical neutral loss database can one or more records, each with a neutral loss value as a key and one or more candidate structures as attributes associated with the key neutral loss value. In these embodiments, the theoretical neutral loss database can be queried with each neutral loss value and any structure(s) retrieved by these queries can be treated as candidate structures.

At block 460, an X-score for each candidate structure can be determined. The X-score can be determined between a given candidate structure and the input spectrum using any suitable scoring scheme, including but not limited to those disclosed in the examples below. For example, an X-score calculation can be a scalar dot product between the material structure with the given candidate structure added and part or all of the input spectrum, perhaps as adjusted with a correction factor.

At block 470, the candidate structure with a best X-score can be selected as a best candidate structure.

At block 480, the material structure can be updated to include the best candidate structure.

At block 490, a determination is made as to whether there are additional input spectra to be processed. If there are additional spectra to be processed, method 400 can proceed to block 420; otherwise, method 300 can proceed to block 492.

At block 492, an output based on the material structure can be generated. The output can include the material structure, the input spectra, some or all of the candidate structures, identifying information and/or other information.

The output can be provided using some or all components of a user interface module, such as user interface module 201, and/or a network communications interface module, such as network communication interface module 202. For example, the output can be displayed on a display, printed, emitted as sound using one or more speakers, and/or transmitted to another device using network communications interface module. Other examples are possible as well.

After completing the procedures of block 492, method 400 can end.

In a second aspect, the present invention provides methods for identification of antibiotic-resistant bacteria, comprising obtaining lipid A from a bacterial sample and determining whether the lipid A comprises a phosphoethanolamine (PEtN) modification and/or a hexosamine modification at the 1 position, wherein presence of PEtN modified-lipid A and/or the hexosamine modification indicates that the bacteria is antibiotic-resistant.

As used herein, a "PEtN modification" comprises the addition of ethanolamine to a lipid A phosphate. In one embodiment, the PEtN modification comprises a modification at the 4' position for *A. baumannii*. In another embodiment, the PEtN modification comprises a modification at the 1' and 4' position for *K. pneumoniae*.

In one embodiment, the antibiotic resistance comprises resistance to colistin (also known as polymyxin E). In another embodiment, the bacterial sample comprises an *Acinetobacter* sample, such as an *A. baumannii* sample. In another embodiment, the bacterial sample comprises a *Klebsiella* sample, such as a *K. pneumoniae* sample.

As shown in the examples that follow, phosphoethanolamine and/or hexosamine modification at the 1 position of lipid A are shown as novel biomarkers for colistin resistance in *A. baumannii* and *K. pneumoniae*. These subtle structural changes shown for these bacterial species commonly occur as a result of environmental perturbations to which the bacteria adapt to avoid host killing mechanisms.

Isolation and analysis of lipid A from the bacteria in this second aspect of the invention can be carried out by any suitable methods, including but not limited to any embodiment or combination of embodiments of the methods described herein.

The sample may be any suitable sample, including but not limited to clinical samples, such as those described above. Also as described above, the lipid A can be obtained directly from the sample, or bacteria in the sample may first be amplified to obtain more cells in order to increase the amount of lipid A obtained.

Generating Theoretical Signature Ion and Theoretical Mass

In a third aspect, the present invention provides methods for constructing libraries of LA and/or LTA precursor ion and $MS^E$ and/or $MS^n$ data, comprising (a) obtaining PIMS spectra on precursor ions for lipid A (LA) or precursors molecules thereof and/or lipoteichoic acid (LTA) or precursor molecules thereof obtained from a plurality of different bacteria;

(b) determining precursor ion m/z values and relative ratios of precursor ion signals relative to each other;

(c) determining consensus values for the precursor ion m/z values and the relative ratios of the precursor ion signals relative to each other for a given bacteria; and (d) storing the consensus values in a database as a feature of the bacteria type.

As disclosed above, the libraries of the invention can be used, for example, for the automatic identification of bacterial species. Accessible information from the library can include: i) bacterial species, bacterial $MS^1$ phenotypes, ii) glycolipid hierarchical tandem mass spectra ($MS^1$ to $MS^n$), iii) annotated glycolipid structures, and iv) theoretical and observed isotopic distributions for the primary precursor ion species in each $MS^1$ data set.

All embodiments and combinations of embodiments, of the first and second aspect of the invention can be used in this third aspect unless the context dictates otherwise. Thus, the methods for extracting/isolating LA or LTA samples from bacteria include but are not limited to any of the methods disclosed herein. Similarly, all embodiments of MS devices/techniques that can be used are equally applicable in this aspect, as are the various embodiments for obtaining PIMS spectra and determining precursor ion m/z values and relative ratios of precursor ion signals relative to each other. In one embodiment, MALDI-TOF-MS and/or SAWN-ITMS$^n$ data in both positive and negative ion modes are used. In one non-limiting example, MALDI-TOF-MS$^1$ data is used (together with data from other MS instrument types) to populate the database with precursor ion (i.e. $MS^1$) data in positive- and negative-ion modes. These $MS^1$ data consist of two columns of numbers, m/z values and relative intensity for each. Acquiring $MS^1$ data on different platforms provide technical replicates of each extract and an understanding of how instrumental differences and operators affect bacterial identification. Additionally, it permits determination of which glycolipid extracts only produce good data in positive ion mode.

For example, suppose two mass spectrometers MS1 and MS2 are used to generate spectra and/or other information to be stored in a database. In this example, suppose MS1 generates spectra using the JCAMP-DX format, while MS2 generates spectra using the mzXML format. Further, suppose that the database uses a third format to store spectra. The database and/or auxiliary software can convert JCAMP-DX and mzXML formatted spectra into the third format for database storage. Then, upon retrieval, the database and/or auxiliary software can reconvert the stored third-format spectra into another format, such as, but not limited to JCAMP-DX or mzXML, for output.

The methods of this aspect of the invention comprise LA or LTA samples from a plurality (2 or more) of different bacteria. The number of different bacteria from which samples are obtained is determined based on user needs. In various embodiments, PIMS data may be obtained from/resulting data stored for two or more different bacteria. As used herein, "different bacteria" are different bacterial species, different sub-species, and/or the same species/sub-species but where some portion have undergone an environmental modification (for example, development of antibiotic resistance).

In one embodiment, PIMS spectra may be obtained from one or more (or all) of the following groups of bacteria, that cannot be distinguished using current ribosomal profiling techniques:

Shigella and E. coli;
S. pneumoniae and S. mitis;
Pseudomonas subspecies including aeruginosa and Stenotrophomonas maltophila;
A. baumanii and A. calcoaceticus;
Enterobacter subspecies including E. asburiae, E. cloacae, E. hormaechei, E. kobei, E. ludwigii, and E. nimipressuralis;
Bordetella pertussis and B. bronchiseptica;
Bacteroides nordii and B. salyersiae;
Candida africana and C. albicans;
Acetinotbacter subspecies; and
Methicillin-resistant Staphylococcus aureus (MRSA) strains and non-methicillin resistant Staphylococcus aureus.

In another embodiment, PIMS spectra may be obtained from two, more, or all of Escherichia coli, Staphylococcus aureus, Staphylococcus epidermidis, Streptococcus pneumoniae, S. mitis, Streptococcus pyogenes, Stenotrophomonas maltophila, Mycobacterium tuberculosis, Neisseria gonorrhoeae, Neisseria meningitidis, Bordetella pertussis, B. bronchioseptica, Enterococcus faecalis, Salmonella typhimurium, Salmonella choleraesuis, Klebsiella pneumoniae, Pseudomonas aeruginosa, Acinetobacter baumannii, A. calcoaceticus, Bacteroides nordii, B. salyersiae, Enterobacter subspecies including E. asburiae, E. cloacae, E. hormaechei, E. kobei, E. ludwigii, and E. nimipressuralis, extended spectrum β-lactamase organisms, as well as bacterium in the genus Acinetobacter, Actinomyces, Bacillus, Bacteroides, Bordetella, Borrelia, Brucella, Clostridium, Corynebacterium, Campylobacter, Deinococcus, Escherichia, Enterobacter, Enterococcus, Erwinia, Eubacterium, Flavobacterium, Francisella, Gluconobacter, Helicobacter, Intrasporangium, Janthinobacterium, Klebsiella, Kingella, Legionella, Leptospira, Mycobacterium, Moraxella, Neisseria, Oscillospira, Proteus, Pseudomonas, Providencia, Rickettsia, Salmonella, Staphylococcus, Shigella, Spirillum, Streptococcus, Stenotrophomonas Treponema, Ureaplasma, Vibrio, Wolinella, Wolbachia, Xanthomonas, Yersinia, and Zoogloea.

In another embodiment, the methods further comprise fragmenting all or a subset of the precursor ions to produce a set of derived fragment ions, and obtaining MS spectra on all or a subset of the derived fragment ions ($MS^n$ or $MS^E$) spectra; determining consensus values for the derived fragment ion m/z values and the relative ratios of the derived fragment ion signals relative to each other for a given bacteria; and storing the consensus values as a feature of the bacterial type in a database. "Derived fragment ions" are described above; all embodiments for obtaining and analyzing $MS^n$ and or $MS^E$ spectra herein are applicable to this third aspect of the invention. In one embodiment, the $MS^n$ spectra data is obtained for at least two generations, $MS^1$ and $MS^2$, of precursor ions ($MS^1$) and derived fragment ions ($MS^2$); in another embodiment, at least three generations $MS^1$, $MS^2$, and $MS^3$, of precursor ions ($MS^1$) and derived fragment ions ($MS^2$ and $MS^3$); etc.

In one non-limiting example, SAWN-ITMS″ data is obtained. Subtle details of strain variation resulting from environmental pressure may be hidden under $MS^1$ isobaric signals. Use of the MS″ approach helps to tease apart all glycolipid structures above a threshold, including those highly similar isobars obscured in $MS^1$ data as a single m/z species. In one embodiment, the threshold is preset threshold. Any suitable threshold can be used, and it is within the level of those of skill in the art to establish a suitable threshold, based on the teachings herein. In one non-limiting embodiment, the threshold would require a minimum signal/noise ratio of 2:1. See, for example, Anal. Chem. 2009 81:6481-8. For glycolipid structure definition the SAWN-ITMS″ platform can be used to acquire positive- and negative-ion $MS^1$ and MS″ data. The MS″ data can be generated for the most abundant ion species (approximately 5-7 species) in each $MS^1$ spectrum and their structures determined using the MS″ methods described in detail above. Structures and all SAWN-ITMS1 and SAWN-ITMS″ data can be recorded in the MSGS library to identify bacteria alone, or in combination with MALDI-TOF-$MS^1$ data.

In another embodiment, the methods further comprise storing in the database as a feature of the bacterial type one or more of signature ions, and LA or LTA structure(s). Signature ions can be determined via standard MS techniques based on the teachings herein; signature ions for some bacterial LA or LTA that are known may be input into the database, for example, manually or through automated access to other databases. Similarly, LA and LTA structures can be determined using the methods of the present invention; previously identified LA or LTA structures may also be input into the database, for example, manually or through automated access to other databases.

In another embodiment, the method comprises storing consensus values for the precursor ion and derived fragment ion m/z values and the relative ratios of the precursor ion derived fragment ion signals relative to each other for a given bacteria in a theoretical neutral loss database, wherein the consensus values are used to assign a dissociation formula for LA or LTA for the different bacterial types. As used herein, dissociation formulae are the pathway(s) of dissociation of a precursor ion. In this embodiment, the method results in a database comprising, for example, a database based on the interpretation of LA and/or LTA fragmentation rules in tandem mass spectra which includes phosphate patterns as well as fatty acid and monosaccharide substituents. Direct bond cleavages of LA and/or LTA structures can be considered as the general template for fragmentation and structural inference. In a further embodiment, each database may comprise two sub-databases (or may comprise two separate but connected databases) for: (1) theoretical signature ions (TSI) and (2) theoretical neutral losses (TNL) (FIGS. 11-13). For example, the observed LA signature ions can be determined from the conserved characteristic of LA diglucosamine and named according to nomenclature known in the art. Based on the observed fragmentation templates of LA, signature ions can be calculated and compared to the theoretical signature ion (TSI) database. In a further embodiment, any MS spectra without any identifiable signature ions are discarded prior to comparing to the database.

To increase the structural diversity of LA and/or LTA represented in the TSI database, a user-defined carbon range of fatty acids can be applied (for example, 12:0 to 20:0 fatty acids). By systematically altering the fatty acid side chain lengths and positions, all possible signature ions can be computed, if desired, and incorporated into the TSI database. To facilitate structure assignment, neutral losses of signature ions can be calculated and put in the theoretical neutral loss (TNL) database. Additionally, common observed neutral losses that come from direct bond cleavages of LA other than cleavages of signature ions can also be included in the TNL database. Similarly, to increase the structural diversity covered by TNL databases, fatty acid compositions of TNL can be systematically altered within the user-defined carbon range.

In this embodiment, acquired MS″ spectra for an unknown bacteria can be searched against the TSI database to find possible signature ions (FIGS. 11-13). Any identified signature ions suggest formulae corresponding to the reducing and/or non-reducing portions of LA. By subtracting the mass of signature ions from their precursors, the neutral losses of signature ions can be subsequently calculated and searched against the TNL database. The combination of signature ions and matched neutral losses may be used to provide a preliminary candidate structure (FIGS. 11-13).

The library structure and reading software can be of any suitable type. In one non-limiting embodiment, the library structure software may be based, for example, on a relational database system (MySQL), and the reading software can be a graphical user interface, such as a web-based user interface. The library can be stored in a MySQL database hosted on a desired secure server. The library structure software is geared toward extracting information from the library for bacterial identification by processing queries for comparison of observed data to previously recorded data. In other embodiments, the library structure software can provide some or all data stored in the theoretical signature ion (TSI) and/or theoretical neutral loss (TNL) database to an application program for processing without use of database queries. For information on the open source software MySQL concept see the articles describing it at web site dev.mysql.com/tech-resources/articles/.

Example 1

$MS^1$ Analyses

Extraction Protocol

Lipid A and LTA were prepared using a published isolation method (*J. Lipid Res.* 46: 1773-1778, 2005). Briefly, approximately 0.1-10 mg of lyophilized material of an overnight culture of each strain was resuspended in 400 µl of isobutyric acid and 1 M ammonium hydroxide (5:3 v:v) and incubated at 100° C. for 30 minutes to 1 h, vortex frequently in a 1.5 ml screw-cap test tube. Individual samples were cooled in ice water and centrifuged for 15 min at 2000×g, supernatants were collected and diluted 1:1 (v:v) with endotoxin-free water. The samples were subsequently frozen and lyophilized overnight. The resultant powered material was washed twice with 1 ml of methanol and the insoluble lipid A was extracted in 100-200 µl of a mixture of chloroform, methanol, and water (3:1:0.25 v:v:v) depending on starting amount.

Mass Spectrometry Procedures

Negative ion matrix assisted laser ionization desorption-time of flight tandem mass spectrometry (MALDI-TOF/TOF MS) experiments was performed. Briefly, lipids were solubilized in 200 µl of a mixture of chloroform, methanol, and water (3:1:0.25 v:v:v) and spotted (1 µL) directly onto the MALDI sample plate, followed by 1 µL of 100 mg/mL norharmane MALDI matrix dissolved in chloroform/methanol/water (3:1.5:0.25, v/v/v). All experiments were performed using a Bruker Autoflex Speed MALDI-TOF/TOF mass spectrometer (Bruker Daltonics Inc., Billerica, Mass., USA). Each spectrum was an average of 300-500 shots and 50-75% laser power. For MS/MS analysis, precursor ions were chosen and submitted for LIFT TOF/TOF acquisition in the negative ion mode as per Bruker standard MALDI-TOF protocols. ES Tuning Mix (Agilent, Palo Alto, Calif., USA) was used as a calibration standard.

Microwave Extraction Protocol (a) Lipid a Isolation from Cells Using Microwave-Assisted Enzymatic Digestion and Sodium Acetate Hydrolysis—Liquid Cultures 200 µl 50 mM of sodium acetate buffer (pH 4.5) containing proteinase K (60 µg/ml) was added to lyophilized cells and microwaved at 50 W for 5 min at 58° C. The samples were incubated for 1 hour at 100° C., followed by centrifugation at 10000 g for 5 min and supernatant discard. The pellet was washed twice with 400 µl methanol, centrifuged at 10000 g for 5 min, dissolved and extracted once with 200 µl chloroform/methanol (1:1, v/v), followed by centrifugation at 8000 g for 5 min, and drying of supernatant under a nitrogen stream.

(b) Lipid a Isolation from a Single Colony Using Microwave Assisted—Agar Plate Cultures Bacterial colony was placed in a 1.5 ml Eppendorf tube containing 1% phenol in PBS, washed twice using 400 µl diH$_2$O, and centrifuged at 10000 g for 5 min. Following this step, the sample was treated as described above for liquid cultures MALDI-TOF Mass Spectra of Gram-Negative and -Positive Bacterial Glycolipid Extracts.

Using a common extraction method (isobutyric acid/ammonium hydroxide) for both Gram-negative and -positive bacterial backgrounds, lipid A and LTA were extracted, respectively and analyzed using a MALDI-TOF-MS in the negative ion mode [29, 36]. Bacteria lipid A (LA) or lipoteichoic acid (LTA) was extracted and isolated from cell membranes and analyzed by MALDI-TOF spectrometer. MS1 spectra were collected and preprocessed as follows. Raw data files were converted to mzXML data format. The peak list information were detected using MassSpecWavelet, a wavelet-based mass spectrum processing software provided by the Bioconductor (Bioinformatics, 2006. 22(17): p. 2059-2065. The similarity of pairs of the spectra was determined by calculating their dot-product.

Figure 5:
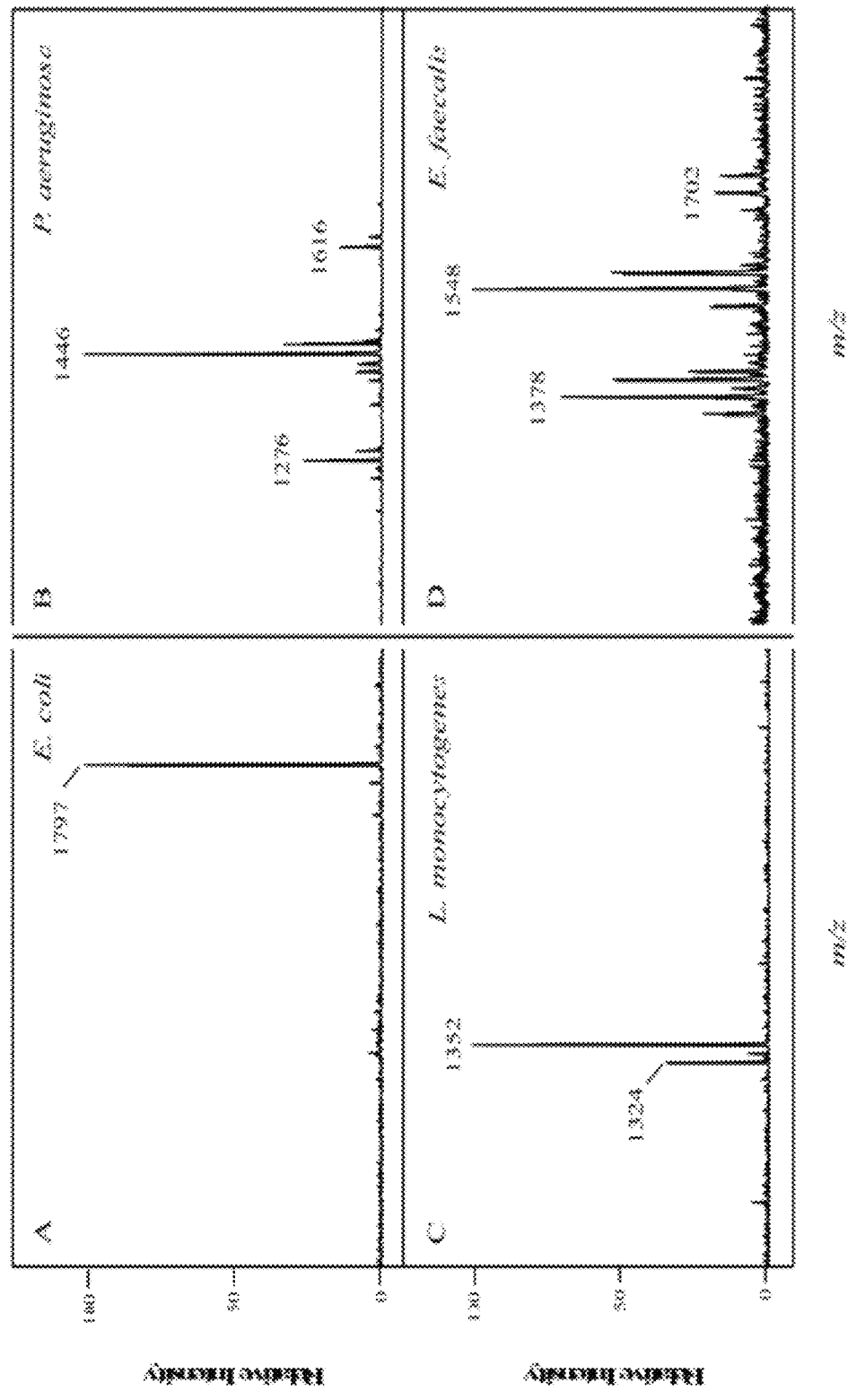
FIG. 5. Representative MALDI-TOF mass spectrum from Gram-negative and -positive bacteria used to generate bacterial glycolipid library. Gram-negative bacteria: (A) *E. coli*, (B) *P. aeruginosa*, and Gram-positive: (C) *L. monocytogenes*, (D) *E. faecalis*. All glycolipid extracts (lipid A and LTA) were generated using a small-scale lipid A extraction method (isobutyric acid/ammonium hydroxide) and mass spectra (MS1) recorded in negative ion mode on a MALD-TOF-MS (Bruker Autoflex Speed).

Spectra shown in FIG. 5 are representative examples for two Gram-negative and -positive bacterial backgrounds. Using these methods of glycolipid extraction and MS analysis, results from approximately 25 additional species and subspecies *were* used to generate the heat map demonstration of glycolipid phenotyping (FIG. 6).

This preliminary data clearly demonstrates the ability of LA and LTA MS1 data to distinguish not only bacteria, but also antibiotic-resistance (MRSA is distinguishable from non-MRSA) and environmental variants (*P. aeruginosa* grown high ($^\S$) and low Mg ($^{\S\S}$), growth conditions known to alter LA composition is distinguishable). As indicated by the diagonal black set of squares all data sets most closely match themselves and not other data. A black square represents a normalized score of 1.0 or a perfect match, while the darkest gray squares represent a score of 0 at the opposite end of the normalized scoring scheme or where there is no match. The intermediate gray color indicates that there is high similarity, but that there are MS features remaining that distinguish these data as unique one from the other. The same is true for the white scores where one can see that a single molecular change can be detected between *A. baumannii* (\*) without modifications from *A. baumannii* with ColR modifications: i.e. additional of PEtN versus hex (\*\*) and *S. flexneri* and *E. coli* O157 can be distinguished. These cases demonstrate that the present methods will succeed where the protein phenotype of Biotyper™ fails.

This data set demonstrates that bacteria may be identified by MS1 profiles of their glycolipid extracts. To provide more objective evidence of the value of this approach, sensitivity (100%), accuracy (96%), and specificity (96%) were calculated using a standard receiver operating characteristic (ROC) curve and a 6-point result rating (data not shown). All 128 true positives in a total of 3,894 cases from the test data were correctly identified with only 145 false positives. Most false positives can be explained by dot-product scores greater than 0.5 but less than 0.8 of either sub-species or modified growth conditions. This confirms the MS1 methods of the invention provide a very sensitive and accurate method for bacterial identification.

Identification of Bacteria from Mixtures:

Using similar methods to those discussed above, *P. aeruginosa, F. novicida* and *E. coli* lipid A extracts were mixed 10:10:1 and a mass spectrum recorded in negative ion mode on a MALD-TOF-MS (Bruker Autoflex Speed). The diversity of various bacterial glycolipid structures form the foundation of LA and LTA chemical barcodes to identify bacteria. Importantly, these glycolipids can constitute up to 90% of the total bacterial membranes and are stable, making them easily and rapidly extractable. Similar unique structures exist for LTA from Gram-positive bacteria. Using the same methods as disclosed above, it was shown (FIG. 7) that mixture analysis is feasible from ordinary MALDI-TOF-MS instrumentation providing an advantage over current protein-based methods that require pure cultures.

Analysis of Lipid A from *A. baumannii* Extracted Directly from a Complex Sample.

To determine if lipid A from *A. baumannii* could be extracted directly from bacteria present in zero passage samples (e.g. human wound effluent and serum), *A. baumannii* ATCC strain 19606 was added or "spiked" to either wound effluent (FIG. 8B) or serum (8C) at approximately $1 \times 10^8$ colony forming units (CFU)/ml. The samples were processed using a small-scale lipid A extraction method (isobutyric acid/ammonium hydroxide) described above. The results show that similar lipid A profiles could be generated using MALDI-TOF-MS from bacteria present in wound effluent or serum, as compared to bacteria alone (FIG. 8A), demonstrating the feasibility of the methods of the invention to identify wound and or bloodstream infection without further growth or amplification in the clinical laboratory.

Analysis of Lipid a from *A. baumannii* Extracted by Microwave-Assisted Extraction Protocols.

Using the microwave glycolipid extraction process described above, lipid A has been extracted in approximately 3.5 hours from single colonies of *Bordetella subspecies, Pseudomonas aeruginosa, Francisella novicida, E. coli*, and *Klebsiella pneumoniae*. The results (data not shown) clearly show the value of this extraction and MS analysis technique in the rapid and sensitive analysis of the glycolipid molecules in these bacterial species.

Prevalence of Modifications to *A. baumannii* Lipid A that Result in Colistin Resistance.

Figure 10:
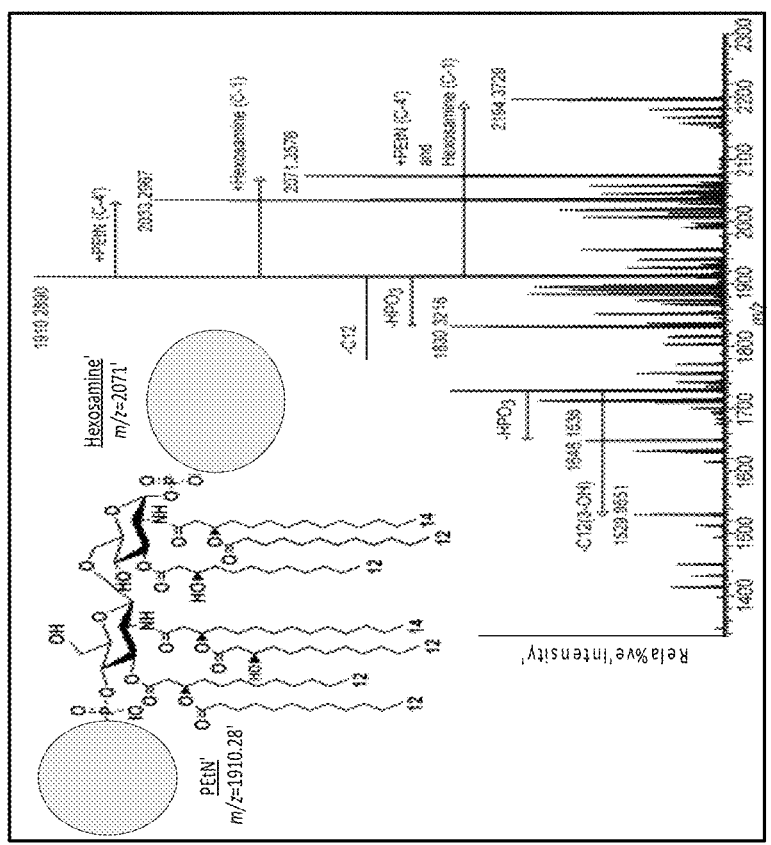

Colistin resistance is rare in *Acinetobacter baumannii*, however wound infections in injured soldiers are becoming a matter of great concern for the US military hospital system. However, due to the prevalence of multidrug antibiotic resistance in a majority of *A. baumannii* clinical isolates, there has been a dramatic increase in the primary use of the negatively charged antimicrobial peptide, colistin (polymyxin E). Even though colistin has been in limited use over the past 30 years due to concerns regarding toxicity, specifically nephrotoxicity (damage to the kidneys) and neurotoxicity (damage to the nerves), little is known about the molecular mechanism of colistin resistance in *A. baumannii*. Though recently alterations in the lipid A content, through the addition of the positively charged moiety, phosphoethanolamine (PEtN) at the 4' position have been reported that alters the electrostatic charge on the bacterial membrane [37]. We have also identified a second positively charged moiety, a hexosamine at the 1 position of lipid A (FIG. 10A).

To test the hypothesis that either or both of these lipid A modifications are important in altering the resistance profile of *A. baumannii* to colistin, lipid A was extracted from a variety of clinical isolates from three geographically distinct patient populations: clinical trial patients at the National Institutes of Health in Bethesda, Md., Wounded Warfighters at Walter Reed Medical Center in Washington, D.C., and in-patients at the Siriraj Hospital, Mahidol University, Bangkok Thailand. Lipid A extraction, MS, and $MS^1$ analysis were performed as described above. Results for an exemplary number of bacterial isolates are shown in FIG. 10B and indicate that the presence of phosphoethanolamine is a novel biomarker for colistin resistance in *A. baumannii*. These subtle structural changes shown for *A. baumannii* commonly occur as a result of environmental perturbations to which the bacteria adapt to avoid host killing mechanisms.

In addition, we have recently obtained five colistin resistant isolates from wounded soldiers at Walter Reed Army Institute of Research (WRAIR) that show a 100% correlation of phosphoethanolamine addition to lipid A in these isolates. These results were reported within 4 hours of the isolates arrival as agar plate cultures in the laboratory. These results clearly demonstrate the feasibility of this type of analysis as a diagnostic test for colistin resistance in a clinical setting and potentially keep a wounded soldier from receiving a treatment that may have detrimental toxic effect with no positive bacterial eradication outcome.

Using identical procedures, it was determined that colistin resistant *K. pneumoniae* possess lipid A modified by PEtN at the 1' and 4' position (data not shown).

Example 2

$MS^n$ Analysis

Infusion-based electrospray ionization (ESI) coupled to multiple-stage tandem mass spectrometry ($MS^n$) is a standard methodology for investigating lipid A structural diversity (Shaffer et al. 2007). Annotation of these $MS^n$ spectra, however, has remained a manual, expert-driven process. In order to keep up with the data acquisition rates of modern instruments, we devised a computational method to annotate lipid A $MS^n$ spectra rapidly and automatically, which we refer to as Hierarchical Tandem Mass Spectrometry (HiTMS) algorithm. As a first-pass tool, HiTMS aids expert interpretation of lipid A $MS^n$ data by providing the analyst with a set of candidate structures that may then be confirmed or rejected. HiTMS deciphers the signature ions (e.g. A-, Y- and Z-type ions) and neutral losses of $MS^n$ spectra using a species-specific library based on general prior structural knowledge of the given lipid A species under investigation. Candidates are selected by calculating the correlation between theoretical and acquired $MS^n$ spectra. At a false discovery rate of less than 0.01, HiTMS correctly assigned 85% of the structures in a library of 133 manually annotated *Francisella tularensis* subspecies *novicida* lipid A structures. Additionally, HiTMS correctly assigned 85% of the structures in a smaller library of lipid A species from *Yersinia pestis* demonstrating that it may be used across species.

Materials and Methods

Preparation of Bacterial Lipid A. *Francisella* tularensis subspecies *novicida* (Fn) strain U112 was grown with aeration in tryptic soy broth (Gibco BRL, Grand Island, N.Y.) supplemented with 0.1% cysteine at 25° C. and harvested in the stationary phase. Yp strain KIM6+ was grown in Luria broth (pH 7.4) at 37° C. with aeration and harvested in the late exponential phase referred to as Yp wild type (Yp_WT) [24]. Lipid A C-1 and C-4' phosphatase, LpxE and LpxF, respectively, have been expression cloned in Fn [25]. The individual plasmids with the structural genes of LpxE or LpxF and an ampicillin resistance gene were incorporated into KIM6+ cell via electroporation [11]. The phosphatase expressing strains were then grown in Luria broth containing 100 µg/ml ampicillin (pH 7.4) at 37° C. with aeration and harvested in the late exponential phase, and designated as Yp_LpxE and Yp_LpxF. Fn and Yp LPS were extracted using the hot phenol/water extraction method as previously described [26]. Lipid A was isolated after LPS was treated with RNase A, DNase I, and proteinase K by the method of Caroff [27].

Mass Spectrometric Analysis. The isolated Fn lipid A was analyzed by electrospray ionization (ESI) in the negative ion mode on a hybrid linear ion trap Fourier transform ion cyclotron resonance (FTICR) mass spectrometer (LTQ-FT) (Thermo Scientific, San Jose, Calif.). Lipid A was prepared at ~0.5 mg/ml in methanol/chloroform (2:1) and infused at 1.0 µl/min into a heated capillary inlet maintained at 400-450° C. $MS^n$ spectra were acquired according to a "target" MS scheme predetermined from previous studies [7]. Briefly, in this scheme fifteen deprotonated molecular ions were selected individually for $MS^2$ for the initial loss of 12:0 (number of carbons:number of double bonds), 14:0, 16:0, 18:0, and 20:0 fatty acids, each of which were determined previously to be esterified through the 2' position fatty acid at the 3-hydroxy position of the lipid A deprotonated anions. Each of the subsequent ions was selected for $MS^3$ for the combined loss of galactosamine and the 3-position 3-hydroxy fatty acid (12:0, 14:0, 16:0, 18:0, and 20:0). Ions representing these combined losses were in turn selected for $MS^4$ and monitored for the observation of $Y_1/Z_1$ ion pairs using 1 minute scan averaging. Each $MS^2$ and $MS^3$ "channel" was selected regardless of product ion spectra observed [28] and only the $MS^4$ were used for the determination of the individual lipid A structures. Ion population in the LTQ was set at 10,000 and collision energies employed for $MS^n$ ranged from 25-35%. For Yp Lipid A, data were acquired on an LTQ-FT Ultra (Thermo Scientific) as described elsewhere [10, 11].

Theoretical Databases Construction. Theoretical database constructor program was written with Perl v5.8.8 (see web site perl.org) built for x86_64-Linux platform. A species-specific theoretical database was constructed based on the manual interpretation of lipid A fragmentation rules in tandem mass spectra which included phosphate patterns as well as fatty acid and monosaccharide substituents. Direct bond cleavages of lipid A structures were considered as the general template for fragmentation and structural inference.

Each species-specific theoretical database contains two sub-databases for: 1) theoretical signature ions (TSI) and 2) theoretical neutral losses (TNL) (FIG. 12). Observed signature ions are unique ions that help hypothesize the molecule's structure. The observed lipid A signature ions were usually determined from the conserved characteristic of lipid A diglucosamine and named according to the nomenclature described by Domon and Costello [29]. Based on the observed fragmentation templates of lipid A, signature ions were calculated and put into the theoretical signature ion (TSI) database. To increase the structural diversity of lipid A represented in the TSI database, a user-defined carbon range of fatty acids was applied (i.e. 12:0 to 20:0 fatty acids). By systematically altering the fatty acid side chain lengths and positions, all possible signature ions were computed and incorporated into the TSI database. To facilitate the structure assignment, neutral losses of signature ions were also calculated and put in the theoretical neutral loss (TNL) database. Additionally, common observed neutral losses that come from direct bond cleavages of lipid A other than cleavages of signature ions were also included in the TNL database. Similarly, to increase the structural diversity covered by TNL databases, fatty acid compositions of TNL were systematically altered within the user-defined carbon range.

DeltaMass is a user assigned HiTMS parameter that defines the mass tolerance used to represent the acceptable mass difference between theoretical and observed ions. DeltaMass was applied in all searches against the TSI and TNL databases using the values consistent with the mass accuracy of the acquired data.

Data Preprocessing. Raw data files were converted into mzXML data format by ReAdW, available in Xcalibur software (Thermo Scientific). The peak information from either individual or averaged mass spectra were then extracted using MassSpecWavelet, a wavelet transform based peak detection software provided by the Bioconductor project (see web site bioconductor.org [30]. Resulting peak information of each $MS^n$ tandem mass spectrum was recorded in a peak list file (referred as $MS^n$ spectra hereafter).

Hierarchical Tandem Mass Spectrometry (HiTMS) Algorithm. HiTMS was implemented in Perl v5.8.8 (see web site perl.org) and run on a 64-bit GNU/Linux platform. Acquired $MS^n$ spectra were searched against TSI database to find possible signature ions and spectra without any identifiable signature ions were discarded (FIG. 11). Any identified signature ions suggest formulae corresponding to the reducing and/or non-reducing portions of lipid A. By subtracting the mass of signature ions from their precursors, the neutral losses of signature ions are subsequently calculated and searched against the TNL database. The combination of signature ions and matched neutral losses provides a preliminary candidate structure (FIG. 13). The calculated neutral losses of all the ions in each spectrum were also searched against the TNL database to provide needed information for spectrum annotation. To each lipid-spectrum match (LSM) an X-score is applied to evaluate the closeness of fit between every $MS^n$ spectrum and its preliminary candidate structures (see Cross Correlation). After preliminary structures were assigned, neutral loss of every $MS^n$ spectrum's precursor ion was calculated in the corresponding $MS^{n-1}$ spectrum and searched against TNL database again to identify the possible dissociation patterns. HiTMS continues the above procedures in an iterative manner until the $MS^1$ level is reached. The final structures are deduced by integrating the information gained from the different levels of $MS^n$ data.

Cross Correlation (X-score). The X-score uses a closeness of fit measurements between an acquired and theoretical tandem mass spectrum similar to SEQUEST xcorr [31, 32]. For every LSM, hypothetical lipid A structure is fragmented in silico based primarily on aforementioned direct bond cleavages, including glycosidic bond cleavages (i.e. A/X, B/Y, C/Z type ions), losses of O- and N-linked acyl chains, losses of phosphate, losses of monosaccharide and perturbations representing combined losses. Fragmentations are later combined into a reconstructed mass spectrum representing the theoretical dissociation of the candidate structure. The peak intensity of each reconstructed mass spectrum is assigned a Boolean value where 1 represents the existence of a fragmentation of such m/z value. The X-score between the acquired mass spectrum and the reconstructed mass spectrum of hypothetical structure is measured as follows:

$$X\text{-score} = x_0 \cdot y'$$

where $$y' = y_0 - \left( \sum_{\tau=-75, \tau \neq 0}^{\tau=+75} y_\tau \right) \Big/ 150$$

Each X-score calculation is a scalar dot product between reconstructed mass spectrum x and the preprocessed acquired mass spectrum y' where $\tau$ is the correction factor, as described in previous publications[31, 32]. DeltaMass is used as the bin size to convert mass spectra into vectors. X-score is used by HiTMS to measure the closeness of fit of every LSM.

On-the-fly Decoy Generation. In the world of proteomics, a decoy database is often employed to help evaluate the significance of peptide spectra matches. A decoy database comprises protein sequences that have been shuffled or reversed, generated from the given target database beforehand or on-the-fly [33-35]. HiTMS uses this target-decoy strategy, generating decoys by shuffling the candidate lipid A structure on-the-fly while analyzing each $MS^n$ spectrum. To avoid destroying the lipid A biochemistry, shuffling only occurs on the position and length of fatty acid side chains. This approach ensures that every decoy lipid A exhibits precisely the same molecular composition and mass as the target (i.e. candidate) lipid A structures. X-score of both candidate and decoy LSM are then calculated to help evaluate the significance.

Results and Discussion

Manual Structural Analysis of Fn Lipid A. In prior work, we demonstrated the power of an infusion-based high-throughput (HTP) hierarchical ESI-$MS^n$ strategy (FIG. 11) to generate lipid A tandem mass spectra [7]. In this strategy each precursor ion and all subsequent fragment ions for each generation up to the $4^{th}$ level were fragmented in an hierarchical $MS^n$ fashion. For example, a precursor ion might generate a set of fragment ions $A_1 \ldots A_n$, where n is the number of fragments produced by precursor ion A. Next, each of these $1^{st}$ generation fragment ions was fragmented to produce a series of $2^{nd}$ generation fragment ions $A_{1,1} \ldots A_{1,m}$ where m is the number of $2^{nd}$ generation fragment ions produced by fragment ion $A_1$ such that the process of continued up to the level of the $4^{th}$ generation where ion intensity generally dropped below the detectable threshold. Thereby each precursor ion had an hierarchical set of tandem mass spectra (similar to a surname genealogical tree that branches out from the progenitor parental line) associated with it (FIG. 13) that could be used to aid structure assignment. While lipid A structures were assigned manually in our prior efforts [7, 10, 11], the objective of the current work was to develop HiTMS, an automated structure assignment algorithm, and demonstrate its effectiveness on two structural different types of lipid A. To this end we first tested HiTMS's accuracy for high throughput structure assignments on a library of 133 unique Fn lipid A structures involving 58 variations of fatty acid combinations. This library consisted of a set of 30 previously published structures [7] and an additional set of 103 unpublished structures, all of which were manually assigned; see Supplemental Table S.1 for new structures. The 133 unique lipid A structures in the library were derived from 49,943 tandem mass spectra (i.e. $MS^1$ up to $MS^4$). While HiTMS is capable of analyzing individually all 49,943 tandem mass spectra, our manually derived library of 133 structures came from 284 unique mass spectra produced by averaging 1 min intervals of infusion data. Here, we focused HiTMS analysis on only these 284 averaged spectra for which structures had been manually confirmed. In order to determine the accuracy of structure assignments by HiTMS the 284 averaged mass spectra including 7 $MS^1$, 16 $MS^2$, 55 $MS^3$ and 206 $MS^4$ spectra, were analyzed by HiTMS in an automated manner.

Species-specific Construction of TSI and TNL Databases. Analogous to the use of species-specific genomic databases in proteomics, HiTMS uses species-specific theoretical databases to identify the origin of fragment ions. These species-specific theoretical databases require some basic knowledge of the lipid A structural configuration under investigation, which may be inferred initially from the precursor ion spectrum. For example, in the case of lipid A isolated from Fn, the theoretical signature ions were derived primarily from Y- and Z-type ions as per Domon and Costello [29]. These theoretical signature ions were deposited in a species-specific Fn-TSI database including the combination of $Y_1/Z_1$ ions with a C-1 phosphate, one of 12:0 to 20:0 fatty acids (where chain length range is user defined) on 2-position, and a potential galactosamine (GalN) substitution on C-1 phosphate. Additionally, the fact that Fn lipid A only has a C-1 phosphate which gives characteristic $Y_1/Z_1$ ions was included as signature ions while cross-ring cleavages were not included. Finally, all theoretical neutral losses that could be generated from direct bond cleavage of Fn lipid A were deposited in Fn-TNL databases, including (n:0)-3-OH ketene, (n:1) ketene, (n:0) acid, GalN, glucosamine (GlcN), and a phosphate group; n is the range of carbon atoms in the fatty acids from 12 to 20. In addition, the neutral losses resulting from glycosidic cleavages were also included in Fn-TNL.

In the case of lipid A isolated from Yp, theoretical signature ions were derived primarily from A-type ions. Unlike Fn, Yp lipid A is diphosphorylated and required unique TSI and TNL databases. The phosphorylation patterns of lipid A in Yp are C-1 and C-4' bisphosphate, C-1 pyrophosphate, and C-4' pyrophosphate [11]. Yp lipid A has also been observed to be heavily modified with up to two aminoarabinose (Ara4N) moieties [10]. At the mammalian host temperature of 37° C., the major Yp lipid A structures consists of a β-1,6-linked diglucosamine backbone with two phosphate groups and four primary 14:0 fatty acids [36-38]. Such tetra-acylated lipid A with four identical fatty acids distributed evenly on the reducing and non-reducing end is likely to result in symmetric lipid A structures. The symmetric pattern of bisphosphorylated lipid A produces B/Y- and C/Z-type ions that fail to distinguish reducing end from non-reducing end. Thus, A-type ions are crucial in Yp structure assignment because they fragment across the reducing glycan and result in distinguishable reducing and non-reducing fragments providing unique signature ions [10, 11].

We also examined two Yp phosphatase mutant strains, LpxE and LpxF, which over express phosphatases resulting in the dephosphorlation of the 1- and 4'-positions, respectively, yielding asymmetric lipid A. To account for this asymmetry, both A-type ions, as well as Y- and Z-type ions were also included in Yp-TSI database to detect a C-1 phosphate modification. In total, the Yp-TSI database consisted of $^{0,2}A_2$, $^{0,4}A_2$, $Y_1$, and $Z_1$ ions with combinations of 0, 1, or 2 phosphates; 0, 1, 2, or 3 primary acyl chains; and 0 or 1 secondary acyl chains, while the range of fatty acid carbons was from 12 to 16. All theoretical neutral losses that can be generated from direct bond cleavage of Yp lipid A were deposited in Yp-TNL databases, including (n:0)-3-OH ketene, (n:1) ketene, (n:0) acid, Ara4N, and up to two phosphate groups; where n is the fatty acid chain length. Possible neutral losses from any signature ions were also calculated and included in Yp-TNL databases. Yp-TSI and Yp-TNL databases were used in structural analysis of Yp_WT, Yp_LpxE and Yp_LpxF datasets.

HiTMS Analysis of Fn Lipid A Mass Spectra. HiTMS analysis begins with the examination of a set of tandem mass spectra from the highest order of $MS^n$ mass spectra available, which by default is the least complex, and works backward toward the precursor ion scan. In the case of the Fn dataset, HiTMS began with $MS^4$ tandem mass spectra, which were examined for the presence of species-specific, theoretical signature ions deposited in the Fn-TSI database. In our dataset of 284 averaged tandem mass spectra, HiTMS found that 147 (71%) of the 206 $MS^4$ tandem mass spectra contained signature ions present in the Fn-TSI database. This meant that these 147 $MS^4$ tandem mass spectra came from lipid A species that were assignable based on the known Fn lipid A biochemistry from which the Fn-TSI database was defined. As confirmation, the assigned tandem mass spectra from the signature ion matches were further evaluated for the presence of expected neutral losses present in the Fn-TNL database. This secondary Fn-TNL database search provided preliminary structural hypotheses for each of the 147 mass spectra that were subsequently evaluated by a cross-correlation (X-score) analysis.

In order to evaluate the significance of a match, HiTMS employed a target-decoy strategy similar to that frequently used in proteomics to evaluate the false discovery rate of peptide tandem mass spectral matches. For each of the 147 assigned $MS^4$ tandem mass spectra, HiTMS generated six on-the-fly decoys by shuffling the positions and lengths of the fatty acid side chains based on the species-specific candidate structure. Decoys had the exact same chemical composition as the candidate structure and maintained lipid A-like fragmentation rules. An X-score, which is a correlation score used to evaluate the closeness of fit between an acquired and a theoretical $MS^n$ spectrum was then calculated for every LSM (as defined in materials and methods) including candidates and decoys.

Figure 14:
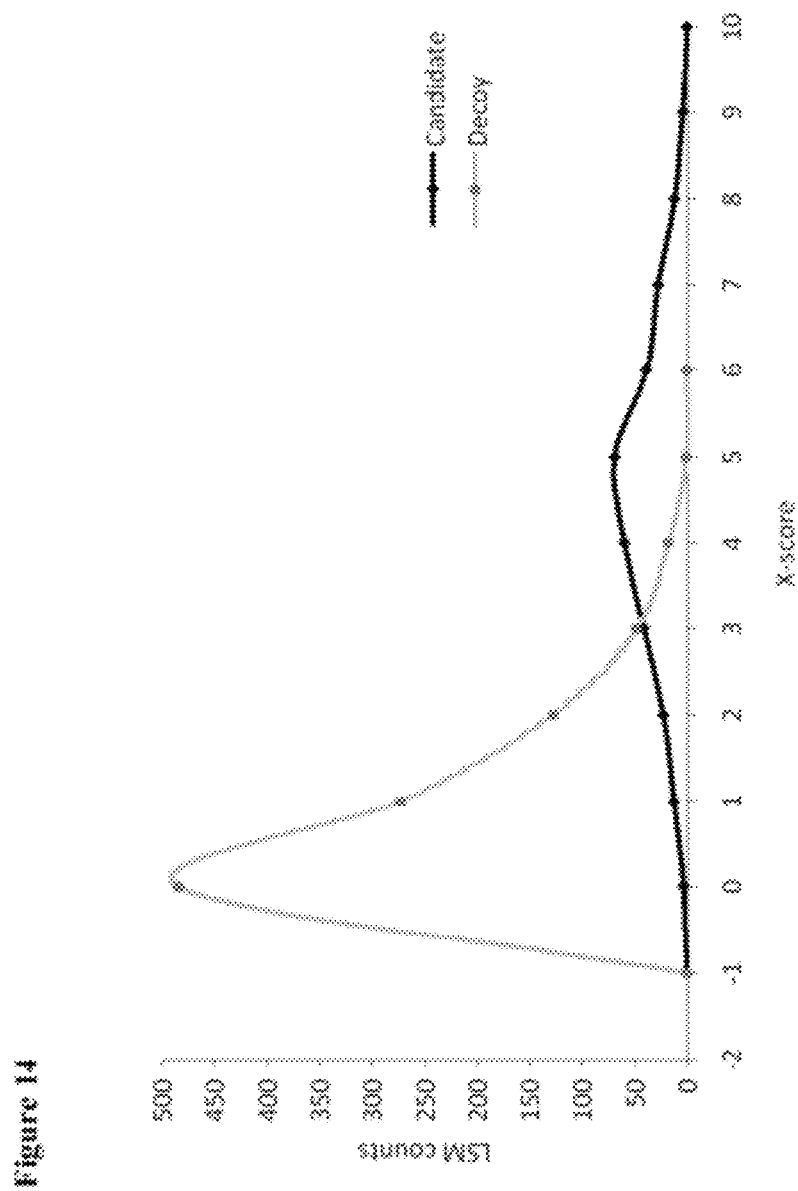
FIG. 14. Example of X-score distribution from the Fn lipid A data. For every MS$^n$ spectrum set, HiTMS generated six decoys on-the-fly based on the candidate structures and calculated the X-score of each lipid-spectrum match (LSM). X-score distribution from candidates was much higher than X-score from decoys that had both median and mean around 0.

The X-score analysis calculated the similarity between tandem mass spectra generated from the derived hypothetical structures used to create the TSI and TNL databases and those from the observed data. To generate the X-scores, peak lists of spectra were converted into vectors binned by DeltaMass mass tolerance (default 0.8 Da). This X-score process produced a set of values similar to those generated by SEUQEST, a popular tool for matching peptide tandem mass spectra to the amino acid sequences of proteins in a database [32]. As shown in FIG. 14, the X-score distribution from candidate matches was much higher than X-score from decoy matches. Thus, an X-score value of 3.0, at which the two distributions intersected, was selected as the default X-score cutoff that successfully rejected more than 99% of decoys and resulting an FDR<0.01.

HiTMS analysis of the 284 averaged mass spectra matched 120 lipid A structures (data not shown). Comparison to our database of 133 manually assigned lipid A structures revealed that 109 unique lipid A structures were correctly retrieved by HiTMS and 11 putative new structures were hypothesized. Only 24 of the original structures were undetected which could be due to a number of reasons; e.g. some of the manually assigned structures may be incorrect or the automated threshold used by HiTMS may have missed some ions selected during the manual analysis. The performance of HiTMS was assessed using F-measure, which is a tool for calculating precision and recall [39]. For the Fn dataset, a balanced F-measure of 0.86 with a precision of 0.91 and a recall of 0.82 was observed which suggests that HiTMS was able to assign lipid A structures with both a high precision and high recall. Interestingly, out of the 206 $MS^4$ total tandem mass spectra 147 were uniquely assignable and 57 annotated with more than one lipid A structure. The latter results suggest the existence of isomers even after the sample was examined down to the $MS^4$ level. The isomeric structures detected in these 57 $MS^4$ spectra are most likely due to various combinations of the fatty acid side chains [7].

HiTMS Versus Manual Annotations. Of the 133 manually assigned lipid A tandem mass spectra, 24 (18%) were not annotated by HiTMS (data not shown). However, while HiTMS produced structural hypotheses for 11 of these 24, their X-scores were below the acceptable cutoff value of 3.0. These low X-score structure predictions could be due to the lack of detectable signature ions or other supporting ions, such as evidence of direct bond cleavage of fatty acids in these 11 tandem mass spectra. It should be noted that as the hierarchical $MS^n$ strategy approaches an $MS^4$ acquisition that data quality naturally declines along with declining ion signal strength. This lower data quality is one likely reason for failing to detect informative signature ions. Thus, as spectral quality decreases, lower X-score values are expected. In addition, reconstruction of theoretical spectra is based on the most ideal fragmentations that include every possible direct bond cleavage and their combinations, not the most likely to cleave chemical bonds. While lipid A structures in Fn are very complex, it may be possible that in some cases the initial spectra might have been misinterpreted manually. For the moment though this manually curated library of structures is the standard from which we judge success for HiTMS. Finally, while we have not done so here, it should be noted that HiTMS is capable of examining individually each of the 49,943 acquired mass spectra that were averaged to produce 248 spectra for manual interpretation. This strategy will likely reveal even more complexity, but given the difficulties in confirming accuracy of so many putative structures we have limited our analysis here to the manually curated data set.

Figure 15:
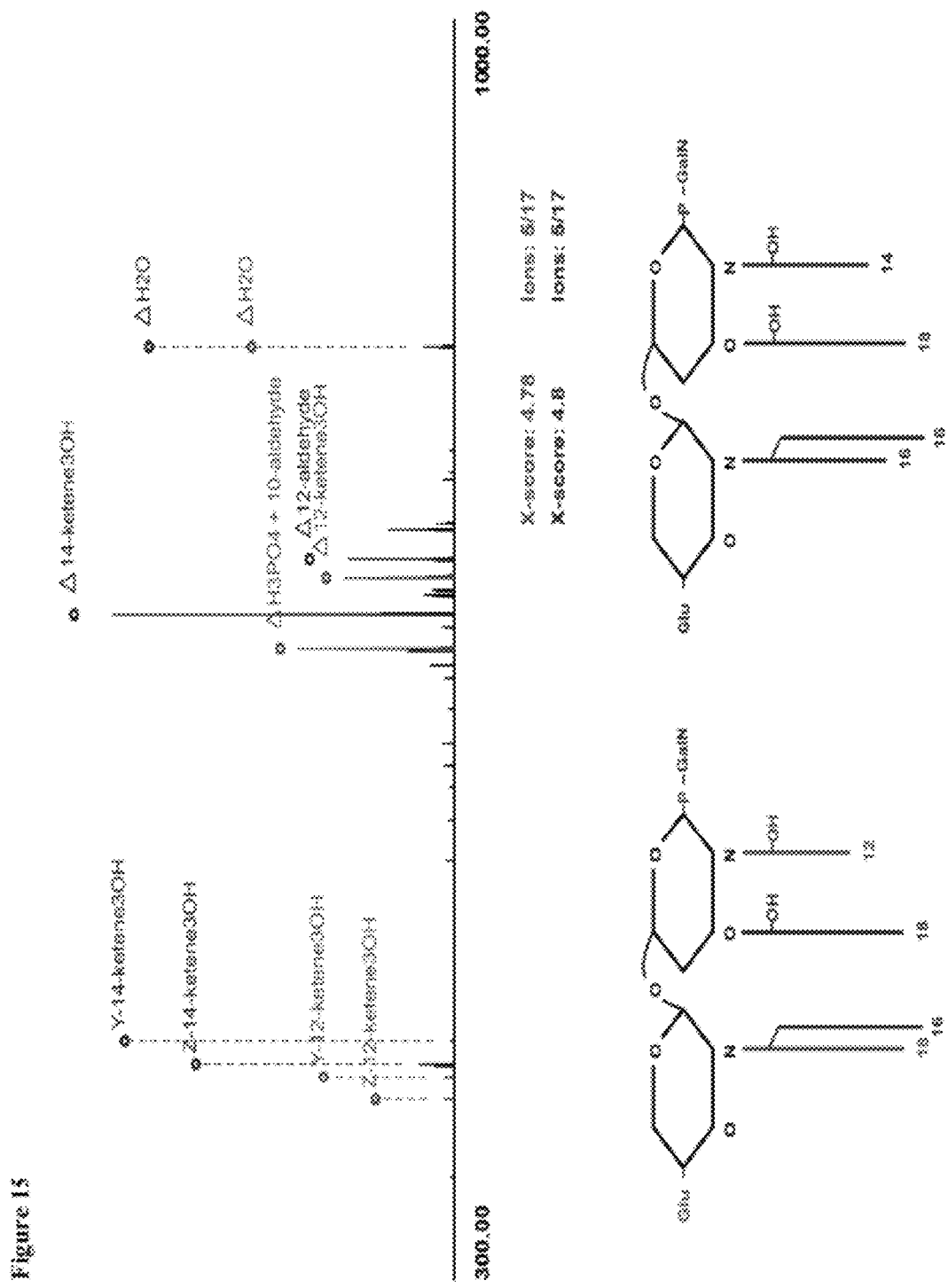
FIG. 15. Example of a putative lipid A structure derived from a MS$^4$ spectrum. (A) Two lipid A isomers were found by HiTMS in MS$^4$ of m/z 1025.7 (from MS$^3$ of 1486.9, from MS$^2$ of 1743.1), including one known lipid A structure (A3_3, blue) and one potential new structure in red. HiTMS labeled signature ions and neutral losses. For example, label "Y-14-ketene3OH" represented a Y-ion with a (14:0)-3-OH fatty acid attached on 2-position, which is equal to a Y-ion backbone plus a (14:0) ketene. Label "Δ" represented a neutral loss of the following molecule. Detected versus theoretical ion ratios are shown next to the X-score of corresponding assignments. (B) Retrieved lipid A structures. Non-black colors indicated the corresponding difference of lipid A. Black indicated the structural information obtained from the neutral losses during MS$^1$ to MS$^2$ and to MS$^3$.

HiTMS Spectral Annotation. As an example of how HiTMS annotates mass spectra in general and the ability of HiTMS to aid manual structure assignment, FIG. 15 shows an annotated tandem mass spectrum and the subsequent lipid A structural hypothesis that, in this case, was not detected by manual interrogation, but can be easily confirmed with the annotated spectrum. Note that one reason this structure may have been missed is due to the low intensity signature ions that HiTMS detected which could be easily neglected during manual assignment due to the fact that there were many more dominant ions to account for during interpretation. Further, as mentioned above, distinguishing isomers is a difficult task that HiTMS analysis of $MS^n$ data was designed to handle. To do so, HiTMS uses a sophisticated peak detection algorithm, MassSpecWavelet [30] to improve the detection of low intensity peaks while allowing the analyst to adjust the threshold accordingly. In these cases, HiTMS not only identified many potential new structures, but also annotated them facilitating manual review of the structure assignments.

Yp Lipid A Structural Analysis. Lipid A structural diversity is reflected, in part, in the various combinations of fatty acids (numbers and types), as well as in the phosphorylation patterns which appear to be species-specific. Like fatty acid composition, phosphorylation pattern has been shown to have strong influence on bacterial pathogenicity [40]. Thus, to insure that HiTMS could make accurate structure assignments where such modifications were common, we also analyzed a previously published Yp lipid A data sets [10, 11]. This data was generated for lipid A isolated from Yp after growth in rich media at 37° C. as part of a study to determine the phosphorylation pattern in Yp. Specifically, Yp lipid A is structurally unique from Fn and has been shown to have diverse phosphorylation patterns including bisphosphorylation and pyrophosphorylation. Unlike Fn, Yp lipid A contains two phosphates and is usually detected in bisphosphorylated forms [10]. In addition, there are additional Ara4N modifications and differences in fatty acid side chains compared to Fn. Thus, this data set on a symmetrical form of lipid A provided a number of unique opportunities to test HiTMS.

These Yp datasets contained $MS^1$ to $MS^3$ tandem mass spectra, but no $MS^4$ tandem mass spectra. Regardless of this difference and the fact that Yp datasets were much smaller than the Fn data set, HiTMS was able to correctly assign two diphosphorylated lipid A structures from Yp_WT dataset (i.e. the major structures) as well as five lipid A structures from genetically modified Yp which resulted from in vivo removal of C-1 phosphate (Yp_LpxE dataset) and C-4' phosphate (Yp_LpxF dataset) [10, 11].

Figure 16:
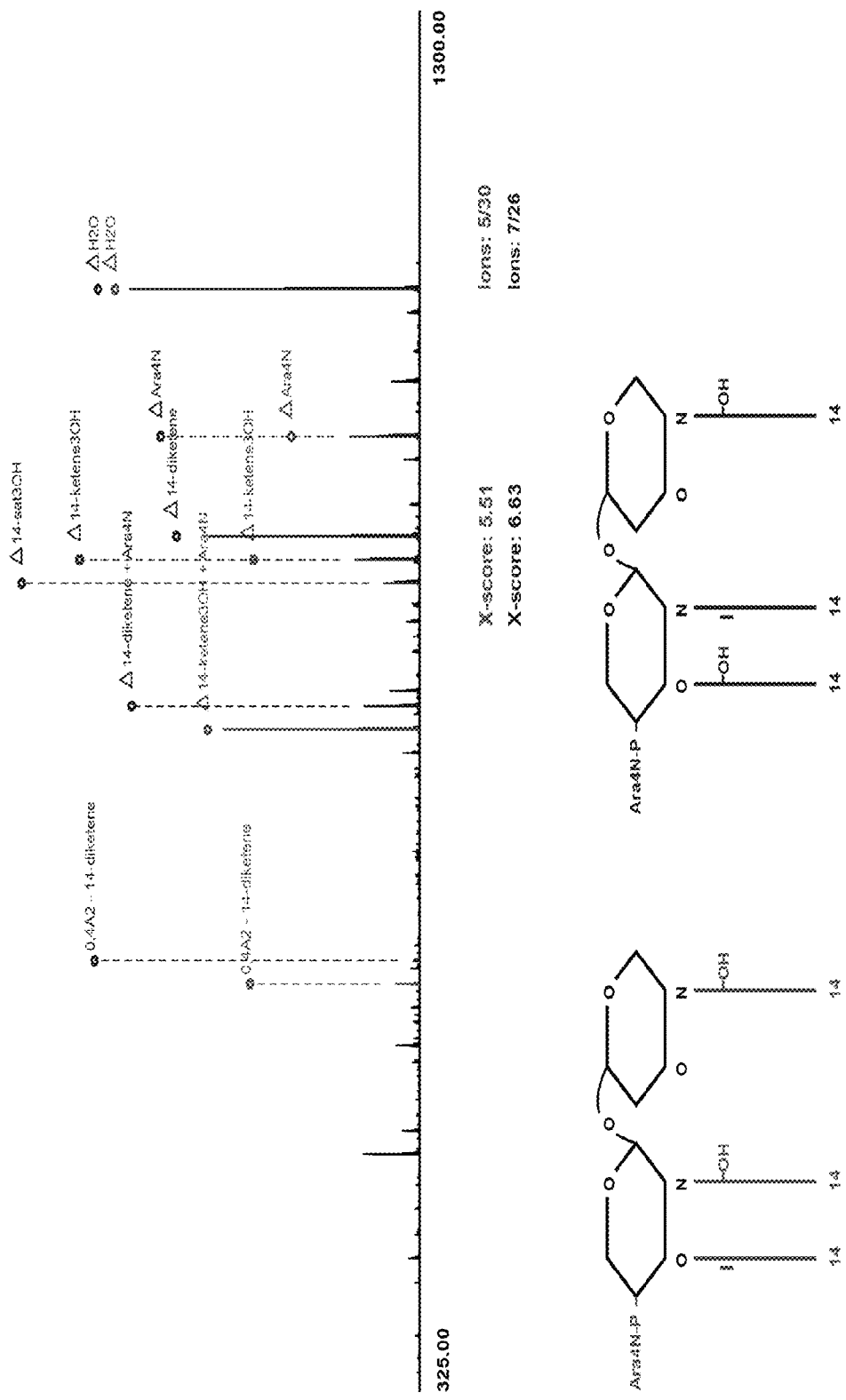
FIG. 16. Example of ambiguous lipid A structural annotations derived from a Yp MS$^3$ spectrum. (A) Negative ion mode ESI-LTQ CID MS$^3$ spectrum of the ion at m/z 1192.7 (from MS$^2$ of 1637.1), from Yp LpxE lipid A. HiTMS proposed two isobaric structures labeled in red and blue. The mass difference of MS$^1$ and MS$^2$ were associated with the combination of a 12:0 fatty acid and a 14:0 ketene or a 12:0 ketene and a 14:0 fatty acid. Label "0,4A2-14-diketene" represented a $^{0,4}A_2$-ion with a (14:1) fatty acid attached on either 2' or 3'-position, which is equal to a $^{0,4}A_2$-ion backbone plus a C14 diketene. Label "Δ" represented a neutral loss of the following molecule. (B) Preliminary lipid A structures proposed by HiTMS. HiTMS did not propose the final structures because of the ambiguous annotation of the neutral losses during $M^1$ to $MS^2$.

Specifically, the Yp data set included spectra from $MS^1$ to $MS^3$ consisting of 31,521 tandem mass spectra in Yp_WT, 2,807 in Yp_LpxE, and 3,187 in Yp_LpxF that were averaged (as per Fn) for HiTMS analysis. Analysis of 148 averaged $MS^3$ spectra from Yp_WT, 35 from Yp_LpxE, and 40 from Yp_LpxF respectively, showed that HiTMS correctly assigned these lipid A structures as well as the structures known to be made by genetically modified LpxE and LpxF phosphatase mutants. As with the Fn data, an X-score cutoff of 3.0 was applied to filter the search results. An example of HiTMS annotation of Yp_LpxE data is depicted in FIG. 16. The detected $^{0,4}A_2$ ion suggests the fatty acid on the 2-position is (14:0)-3-OH, but the fragmentation of unsaturated 14:1 fatty acid could be on 2'- or 3'-position. This process produced two candidate structures, which are presented for expert review to confirm/refute the proposed structures. Based on the X-score and the number of matched ions, the 14:1 acyl chain structure is more likely to be on the 2'-position, however, the possibility of it being on the 3'-position could not be ruled out. In addition, the mass difference from $MS^1$ to $MS^2$ was annotated with a fatty acid composition of a 12:0 plus a (14:0)-3-OH ketene or a 14:0 fatty acid plus a (12:0)-3-OH ketene. In this case, a simple mass difference alone is not enough to determine which composition is more likely correct, but we have shown that HiTMS can annotate correctly even the correlated $MS^2$ spectra provided by A-ions.

Conclusions

The HTP hierarchical $MS^n$ data acquisition strategy we developed previously [7] produced thousands of tandem mass spectra in a few days time that were reduced to one-minute averages for manual interpretation. Even then, Fn lipid A interpretation required several months of expert analysis time to produce 133 unique lipid A structures. Thirty of these 133 were previously reported and here we reported 103 additional structures (data not shown) derived from manual interpretation of the same original dataset. In order to automate lipid A structure assignment so that annotation rates would be more in line with the data acquisition rates, we developed HiTMS. This automated algorithm relies on species-specific theoretical libraries of signature ions and neutral losses to produce structure assignments. HiTMS correctly identified 85% of the 133 structures in our Fn lipid A library at <0.01 FDR and produced 11 hypothesized structures not revealed by manual analysis. These additional structures are likely due to the sensitivity of an automated routine to assign confidence to low intensity signals that manual analysis overlooked. Finally, HiTMS was also shown to work on the Yp lipid A data acquired up to the MS$^3$ level. Thus, HiTMS has been shown to be a reliable tool for systematic, automated interpretation of hierarchical MS$^n$ lipid A tandem mass spectral data sets and capable of proposing structures not considered by manual analysis. The success of HiTMS to assign the structures of two chemically distinct species of lipid A from Fn and Yp species suggests lipid A from other species could also be interpreted via HiTMS, as well as other classes of more generic glycolipids. This expectation is based on the use of an unbiased, scrambled fatty acid composition permutation strategy that is similar to the amino acid sequence scrambling strategy used to assign FDR values in proteomic experiments. This type of analysis provides the user with fast structure assignments based on objectively assigned X-scores at a user defined FDR or a X-score threshold that is applicable for both symmetric and asymmetric lipid A species. Unlike other lipid identification related software that primarily examine lipid classification and lipidomic profiles, HiTMS is capable of analyzing thousands of tandem mass spectra generated by a HTP hierarchical MS$^n$ data acquisition strategy. Finally, while we have used HiTMS on lipid A from well studied species, it also has the potential to be used to examine lipid A data from novel bacteria by empirically optimizing the libraries in an iterative fashion at a given X-score cutoff.

REFERENCES

1. Miller, S. I.; Ernst, R. K.; Bader, M. W., LPS, TLR4 and infectious disease diversity. *Nat Rev Microbiol* 2005, 3, (1), 36-46.
2. Raetz, C. R.; Whitfield, C., Lipopolysaccharide endotoxins. *Annu Rev Biochem* 2002, 71, 635-700.
3. Ernst, R. K.; Yi, E. C.; Guo, L.; Lim, K. B.; Burns, J. L.; Hackett, M.; Miller, S. I., Specific lipopolysaccharide found in cystic fibrosis airway *Pseudomonas aeruginosa*. *Science* 1999, 286, (5444), 1561-5.
4. Ernst, R. K.; Hajjar, A. M.; Tsai, J. H.; Moskowitz, S. M.; Wilson, C. B.; Miller, S. I., *Pseudomonas aeruginosa* lipid A diversity and its recognition by Toll-like receptor 4. *J Endotoxin Res* 2003, 9, (6), 395-400.
5. Hornef, M. W.; Wick, M. J.; Rhen, M.; Normark, S., Bacterial strategies for overcoming host innate and adaptive immune responses. *Nat Immunol* 2002, 3, (11), 1033-40.
6. Coats, S. R.; Jones, J. W.; Do, C. T.; Braham, P. H.; Bainbridge, B. W.; To, T. T.; Goodlett, D. R.; Ernst, R. K.; Darveau, R. P., Human Toll-like receptor 4 responses to *P. gingivalis* are regulated by lipid A 1- and 4'-phosphatase activities. *Cell Microbiol* 2009, 11, (11), 1587-99.
7. Shaffer, S. A.; Harvey, M. D.; Goodlett, D. R.; Ernst, R. K., Structural heterogeneity and environmentally regulated remodeling of *Francisella tularensis* subspecies *novicida* lipid A characterized by tandem mass spectrometry. *J Am Soc Mass Spectrom* 2007, 18, (6), 1080-92.
8. Schneiter, R.; Brugger, B.; Sandhoff, R.; Zellnig, G.; Leber, A.; Lampl, M.; Athenstaedt, K.; Hrastnik, C.; Eder, S.; Daum, G.; Paltauf, F.; Wieland, F. T.; Kohlwein, S. D., Electrospray ionization tandem mass spectrometry (ESI-MS/MS) analysis of the lipid molecular species composition of yeast subcellular membranes reveals acyl chain-based sorting/remodeling of distinct molecular species en route to the plasma membrane. *J Cell Biol* 1999, 146, (4), 741-54.
9. Han, X.; Gross, R. W., Shotgun lipidomics: electrospray ionization mass spectrometric analysis and quantitation of cellular lipidomes directly from crude extracts of biological samples. *Mass Spectrom Rev* 2005, 24, (3), 367-412.
10. Jones, J. W.; Shaffer, S. A.; Ernst, R. K.; Goodlett, D. R.; Turecek, F., Determination of pyrophosphorylated forms of lipid A in Gram-negative bacteria using a multivaried mass spectrometric approach. *Proc Natl Acad Sci USA* 2008, 105, (35), 12742-7.
11. Jones, J. W.; Cohen, I. E.; Turecek, F.; Goodlett, D. R.; Ernst, R. K., Comprehensive structure characterization of lipid A extracted from *Yersinia pestis* for determination of its phosphorylation configuration. *J Am Soc Mass Spectrom* 2010, 21, (5), 785-99.
12. Wenk, M. R., The emerging field of lipidomics. *Nat Rev Drug Discov* 2005, 4, (7), 594-610.
13. Schwudke, D.; Oegema, J.; Burton, L.; Entchev, E.; Hannich, J. T.; Ejsing, C. S.; Kurzchalia, T.; Shevchenko, A., Lipid profiling by multiple precursor and neutral loss scanning driven by the data-dependent acquisition. *Anal Chem* 2006, 78, (2), 585-95.
14. Leavell, M. D.; Leary, J. A., Fatty acid analysis tool (FAAT): An FT-ICR MS lipid analysis algorithm. *Anal Chem* 2006, 78, (15), 5497-503.
15. Ekroos, K.; Chernushevich, I. V.; Simons, K.; Shevchenko, A., Quantitative profiling of phospholipids by multiple precursor ion scanning on a hybrid quadrupole time-of-flight mass spectrometer. *Anal Chem* 2002, 74, (5), 941-9.
16. Ejsing, C. S.; Duchoslav, E.; Sampaio, J.; Simons, K.; Bonner, R.; Thiele, C.; Ekroos, K.; Shevchenko, A., Automated identification and quantification of glycerophospholipid molecular species by multiple precursor ion scanning *Anal Chem* 2006, 78, (17), 6202-14.
17. Song, H.; Hsu, F. F.; Ladenson, J.; Turk, J., Algorithm for processing raw mass spectrometric data to identify and quantitate complex lipid molecular species in mixtures by data-dependent scanning and fragment ion database searching. *J Am Soc Mass Spectrom* 2007, 18, (10), 1848-58.
18. Hubner, G.; Crone, C.; Lindner, B., lipID—a software tool for automated assignment of lipids in mass spectra. *J Mass Spectrom* 2009, 44, (12), 1676-83.
19. Yang, K.; Cheng, H.; Gross, R. W.; Han, X., Automated lipid identification and quantification by multidimensional mass spectrometry-based shotgun lipidomics. *Anal Chem* 2009, 81, (11), 4356-68.
20. Han, X.; Gross, R. W., Shotgun lipidomics: multidimensional MS analysis of cellular lipidomes. *Expert Rev Proteomics* 2005, 2, (2), 253-64.
21. Han, X.; Yang, J.; Cheng, H.; Ye, H.; Gross, R. W., Toward fingerprinting cellular lipidomes directly from biological samples by two-dimensional electrospray ionization mass spectrometry. *Anal Biochem* 2004, 330, (2), 317-31.
22. Mikhail, I.; Yildirim, H. H.; Lindahl, E. C.; Schweda, E. K., Structural characterization of lipid A from nontypeable and type f *Haemophilus influenzae*: variability of fatty acid substitution. *Anal Biochem* 2005, 340, (2), 303-16.
23. Schilling, B.; McLendon, M. K.; Phillips, N. J.; Apicella, M. A.; Gibson, B. W., Characterization of lipid A acylation patterns in *Francisella tularensis, Francisella novicida*, and *Francisella philomiragia* using multiple-stage mass spectrometry and matrix-assisted laser desorption/ionization on an intermediate vacuum source linear ion trap. *Anal Chem* 2007, 79, (3), 1034-42.
24. Une, T.; Brubaker, R. R., In vivo comparison of avirulent Vwa- and Pgm- or Pstr phenotypes of yersiniae. *Infect Immun* 1984, 43, (3), 895-900.

25. Wang, X.; McGrath, S. C.; Cotter, R. J.; Raetz, C. R., Expression cloning and periplasmic orientation of the *Francisella novicida* lipid A 4'-phosphatase LpxF. *J Biol Chem* 2006, 281, (14), 9321-30.
26. Westphal, O.; Jann, K., Bacterial Lipopolysaccharides: Extraction with Phenol-Water and Further Applications of the Procedure. *Methods Carbohydr. Chem.* 1965, (5), 83-91.
27. Caroff, M.; Tacken, A.; Szabo, L., Detergent-accelerated hydrolysis of bacterial endotoxins and determination of the anomeric configuration of the glycosyl phosphate present in the "isolated lipid A" fragment of the *Bordetella pertussis* endotoxin. *Carbohydr Res* 1988, 175, (2), 273-82.
28. Panchaud, A.; Scherl, A.; Shaffer, S. A.; von Haller, P. D.; Kulasekara, H. D.; Miller, S. I.; Goodlett, D. R., Precursor acquisition independent from ion count: how to dive deeper into the proteomics ocean. *Anal Chem* 2009, 81, (15), 6481-8.
29. Domon, B.; Costello, C. E., A Systematic Nomenclature for Carbohydrate Fragmentations in FAB-MS/MS Spectra of Glycoconjugates. *Glycoconjugate Journal* 1988, 5, 397-409.
30. Du, P.; Kibbe, W. A.; Lin, S. M., Improved peak detection in mass spectrum by incorporating continuous wavelet transform-based pattern matching. *Bioinformatics* 2006, 22, (17), 2059-65.
31. Eng, J. K.; McCormack, A. L.; Yates, J. R., An approach to correlate tandem mass spectral data of peptides with amino acid sequences in a protein database. *J Am Soc Mass Spectrom* 1994, 5, (11), 976-989
32. Eng, J. K.; Fischer, B.; Grossmann, J.; Maccoss, M. J., A fast SEQUEST cross correlation algorithm. *J Proteome Res* 2008, 7, (10), 4598-602.
33. Moore, R. E.; Young, M. K.; Lee, T. D., Qscore: an algorithm for evaluating SEQUEST database search results. *J Am Soc Mass Spectrom* 2002, 13, (4), 378-86.
34. Klammer, A. A.; MacCoss, M. J., Effects of modified digestion schemes on the identification of proteins from complex mixtures. *J Proteome Res* 2006, 5, (3), 695-700.
35. Park, C. Y.; Klammer, A. A.; Kall, L.; MacCoss, M. J.; Noble, W. S., Rapid and accurate peptide identification from tandem mass spectra. *J Proteome Res* 2008, 7, (7), 3022-7.
36. Rebeil, R.; Ernst, R. K.; Gowen, B. B.; Miller, S. I.; Hinnebusch, B. J., Variation in lipid A structure in the pathogenic yersiniae. *Mol Microbiol* 2004, 52, (5), 1363-73.
37. Kawahara, K.; Tsukano, H.; Watanabe, H.; Lindner, B.; Matsuura, M., Modification of the structure and activity of lipid A in *Yersinia pestis* lipopolysaccharide by growth temperature. *Infect Immun* 2002, 70, (8), 4092-8.
38. Knirel, Y. A.; Lindner, B.; Vinogradov, E. V.; Kocharova, N. A.; Senchenkova, S. N.; Shaikhutdinova, R. Z.; Dentovskaya, S. V.; Fursova, N. K.; Bakhteeva, I. V.; Titareva, G. M.; Balakhonov, S. V.; Holst, O.; Gremyakova, T. A.; Pier, G. B.; Anisimov, A. P., Temperature-dependent variations and intraspecies diversity of the structure of the lipopolysaccharide of *Yersinia pestis*. *Biochemistry* 2005, 44, (5), 1731-43.
39. Makhoul, J.; Kubala, F.; Schwartz, R.; Weischedel, R., Performance Measures for Information Extraction. 1999, 249-254.
40. Park, B. S.; Song, D. H.; Kim, H. M.; Choi, B. S.; Lee, H.; Lee, J. O., The structural basis of lipopolysaccharide recognition by the TLR4-MD-2 complex. *Nature* 2009, 458, (7242), 1191-5.

We claim:

1. A method for identifying bacteria to at least the genus level of classification, comprising
    (a) loading a sample containing bacteria or a bacterial extract into a mass spectrometer instrument;
    (b) vaporizing the sample of (a);
    (c) ionizing the vaporized sample of (b) to produce precursor ions;
    (d) separating the precursor ions of (c) according to the mass-to-charge ratio;
    (e) detecting separated ions of (d) having values of between about 1000 m/z and about 2200 m/z;
    (f) preparing precursor ion mass spectrometry (PIMS) spectra on the detected ions of (e), wherein the precursor ions are precursor ions of (i) lipid A (LA) or parent glycolipids thereof, or (ii) lipoteichoic acid (LTA) or parent glycolipids thereof, or both (i) and (ii), and wherein the PIMS spectra is PIMS spectra for (i) or (ii), or both (i) and (ii); and
    (g) identifying bacteria in the sample to at least the genus level of classification by comparing the PIMS spectra prepared in (f) to a database of bacterial PIMS spectra.

2. The method of claim 1, wherein the comparing comprises comparing precursor ion m/z values and relative abundance of the precursor ions to the database of bacterial LA and/or LTA PIMS spectra data.

3. The method of claim 1, further comprising fragmenting all or a subset of the precursor ions to produce an $MS^E$ set of ions, and obtaining MS spectra on all or a subset of the $MS^E$ set of ions ($MS^E$ MS spectra), and wherein the comparing further comprises comparing the $MS^E$ MS spectra to bacterial LA and LTA $MS^E$ MS spectra in a database to assist in identifying bacteria in the sample.

4. The method of claim 1, further comprising fragmenting all or a subset of the precursor ions to produce a $MS^n$ set of derived fragment ions, and obtaining MS spectra on all or a subset of the derived fragment ions ($MS^n$ MS spectra), and wherein the comparing further comprises sequentially comparing the $MS^n$ MS spectra to bacterial LA and LTA $MS^n$ MS spectra in a database to assist in identifying bacteria in the sample.

5. The method of claim 4, further comprising searching the PIMS and/or $MS^n$ MS spectra against a database of bacterial LA and LTA signature ions to identify signature ions in the PIMS and/or $MS^n$ MS spectra.

6. The method of claim 5, further comprising
    (i) searching neutral losses of signature ions in the $MS^n$ MS spectra against a theoretical neutral loss database to identify dissociation formulae;
    (ii) proposing LA and/or LTA candidate structures from bacteria in the sample based on the dissociation formulae and the signature ions in the $MS^n$ MS spectra;
    (iii) assigning a score to each LA and/or LTA candidate structure based on correlation between theoretical and acquired $MS^n$ MS spectra, wherein candidate structures that meet or exceed a user-defined threshold are considered as accurate assignments.

7. The method of claim 6, wherein step (i) comprises
    (A) determining a neutral loss of every $MS^n$ MS spectrum's precursor ion in the corresponding $MS^{n-1}$ MS spectrum and searching against the theoretical neutral loss database; and
    (B) iteratively repeating step (A) until level $MS^1$ is reached; and
    wherein step (ii) comprises proposing the LA and/or the LTA structures from the bacteria in the sample based on the integrating data from each $MS^n$ MS level.

8. The method of claim 6, wherein step (iii) comprises
(A) fragmenting the LA and/or the LTA candidate structures by direct bond cleavage to produce fragmentations;
(B) combining the fragmentations into a reconstructed mass spectra representing the theoretical dissociation of the LA and/or the LTA candidate structures; and
(C) assigning the score to each of the LA and/or the LTA candidate structure based on correlation between theoretical $MS^n$ MS spectra and the reconstructed mass spectra.

9. A method for constructing libraries of LA and/or LTA precursor ion and $MS^E$ and/or $MS^n$ data, comprising
(a) loading a sample containing one or more known bacteria or an extract of one or more known bacteria into a mass spectrometer instrument;
(b) vaporizing the sample of (a);
(c) ionizing the vaporized sample of (b) to produce precursor ions;
(d) separating the precursor ions of (c) according to the mass-to-charge ratio;
(e) detecting separated ions of (d) having values of between about 1000 m/z and about 2200 m/z;
(f) preparing PIMS on the detected ions of (e), wherein the precursor ions Are precursor ions of (i) lipid A (LA) or parent glycolipids thereof, or (ii) lipoteichoic acid (LTA) or parent glycolipids thereof, or both (i) and (ii), and wherein the PIMS spectra is PIMS spectra for (i) or (ii), or both (i) and (ii);
(g) determining precursor ion m/z values and relative ratios of precursor ion signals relative to each other from the PIMS spectra of (f);
(h) determining consensus values for the precursor ion m/z values and the relative ratios of the precursor ion signals relative to each other for a given bacteria; and
(i) storing the consensus values in a database as a feature of the bacteria type.

10. The method of claim 1, further comprising
(h) performing mass spectrometry (MS) on precursor ions for bacterial proteins in the sample, to produce protein MS spectra for the precursor ions;
(i) comparing the protein MS spectra to a database of bacterial protein PIMS spectra;
wherein the comparing is used to help identify bacteria in the sample.

* * * * *